(12) United States Patent
Yu et al.

(10) Patent No.: US 8,952,333 B2
(45) Date of Patent: Feb. 10, 2015

(54) METHODS FOR IMPROVED SINGLE PHOTON EMISSION COMPUTED TOMOGRAPHY USING EXACT AND STABLE REGION OF INTEREST RECONSTRUCTIONS

(75) Inventors: Hengyong Yu, Winston-Salem, NC (US); Ge Wang, Blacksburg, VA (US); Ming Jiang, Beijing (CN); Jiansheng Yang, Beijing (CN)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 1074 days.

(21) Appl. No.: 12/938,303

(22) Filed: Nov. 2, 2010

(65) Prior Publication Data
US 2011/0105880 A1 May 5, 2011

Related U.S. Application Data

(60) Provisional application No. 61/257,443, filed on Nov. 2, 2009.

(51) Int. Cl.
*G06T 11/00* (2006.01)
*A61B 6/03* (2006.01)

(52) U.S. Cl.
CPC .............. *A61B 6/037* (2013.01); *G06T 11/006* (2013.01); *G06T 2211/416* (2013.01)
USPC .................................................... 250/363.03

(58) Field of Classification Search
CPC ................................ A61B 6/037; G06T 11/06
USPC ................ 250/363.03, 393, 394, 395; 378/19
See application file for complete search history.

(56) References Cited

U.S. PATENT DOCUMENTS 5,408,511 A * 4/1995 Grangeat et al. ................ 378/19
6,539,103 B1 * 3/2003 Panin et al. .................... 382/131

(Continued)

FOREIGN PATENT DOCUMENTS

WO 2010/141839 A 12/2010

OTHER PUBLICATIONS

Candes, E. and J. Romberg. Signal Recovery from Random Projections. in Computational Imaging III, Proceedings of SPIE vol. 5674, 2005, 11 pages.

(Continued)

*Primary Examiner* — David Porta
*Assistant Examiner* — Faye Boosalis
(74) *Attorney, Agent, or Firm* — New River Valley IP Law, PC; Michele L. Mayberry

(57) ABSTRACT

The present invention provides systems, methods, and devices for improved computed tomography (CT) and, more specifically, to methods for improved single photon computed tomography (SPECT) using exact and stable region of interest (ROI) reconstructions. This technology can be extended across all tomographic modalities. Embodiments provide a method and a system for reconstructing an image from projection data provided by a single photon emission computed tomography scanner comprising: identifying a region of interest in an object; defining an attenuation coefficient and object boundary; computing the generalized Hilbert transform of the data through the defined region of interest and a known subregion; and reconstructing the image with improved temporal resolution at lower radiation doses, wherein the reconstructing comprises performing a reconstruction method that yields an exact and stable reconstruction. Embodiments also provide a method and a system for reconstructing an image from projection data provided by a single photon emission computed tomography scanner comprising: identifying a region of interest in an object; defining an attenuation coefficient and object boundary; and reconstructing the images by minimizing the high order total variation while minimizing the data discrepancy.

38 Claims, 14 Drawing Sheets

(56) References Cited

U.S. PATENT DOCUMENTS

| | | | |
|---|---|---|---|
| 7,853,309 B2 | 12/2010 | Ichihara et al. | |
| 8,121,249 B2 | 2/2012 | Wang et al. | |
| 8,294,109 B2* | 10/2012 | Vija | 250/363.04 |
| 8,483,351 B2 | 7/2013 | Wang et al. | |
| 8,565,860 B2 | 10/2013 | Kimchy et al. | |
| 2005/0211909 A1* | 9/2005 | Smith | 250/393 |
| 2010/0310037 A1 | 12/2010 | Wang et al. | |
| 2011/0142316 A1 | 6/2011 | Wang et al. | |
| 2011/0282181 A1 | 11/2011 | Wang et al. | |
| 2012/0039434 A1 | 2/2012 | Wang et al. | |

OTHER PUBLICATIONS

Candes, E.J.; J. Romberg, and T. Tao, Robust uncertainty principles: Exact signal reconstruction from highly incomplete frequency information. IEEE Transactions on Information Theory, 2006. 52(2): p. 489-509.

Co-Pending International Application No. PCT/US10/37432 filed Jun. 4, 2010, published as WO 2010/141839 on Dec. 9, 2010.

Courdurier M. Restricted measurements for the X-ray transform. Doctoral Dissertation, University of Washington, Seattle, 2007, 60 pages.

Courdurier, M. et al., Solving the interior problem of computed tomography using a priori knowledge. Inverse Problems, 2008. 24, Article ID 065001, 27 pages.

Defrise M et al. Truncated Hilbert transform and image reconstruction from limited tomographic data. Inverse Problems 2006; 22(3):1037-1053.

Donoho, D.L., Compressed sensing. IEEE Transactions on Information Theory, 2006. 52(4): p. 1289-1306.

Hamaker, C. et al., The Divergent beam X-ray transform. Rocky Mountain Journal of Mathematics, 1980. 10(1): p. 253-283.

Han, W.M.; H.Y. Yu, and G. Wang, A total variation minimization theorem for compressed sensing based tomography. International Journal of Biomedical Imaging, 2009, Article ID:125871, 3 pages.

Hansen PC. Regularization, GSVD and truncated GSVD. BIT 1989; 29(3):491-504.

Hansen PC. Truncated singular value decomposition solutions to discrete ill-posed problems with ill-determined numerical rank. SIAM Journal on Scientific and Statistical Computing 1990; 11(3):503-518.

Harten, A. et al., Uniformly high order accurate essentially non-oscillatory schemes .3. Journal of Computational Physics, 1987. 71(2): p. 231-303.

Huang, Q., et al., Reconstruction from uniformly attenuated SPECT projection data using the DBH method. IEEE Transactions on Medical Imaging, 2009. 28(1): p. 17-29.

Kudo H et al. Tiny a priori knowledge solves the interior problem. 2007 IEEE Nuclear Science Symposium and Medical Imaging, Honolulu, Hawaii, Oct. 28-Nov. 3, 2007; 4068-4075. Paper No. M21-1.

Kudo, H.; M. Courdurier, F. Noo, and M. Defrise, "Tiny a priori knowledge solves the interior problem in computed tomography," Phys. Med. Biol, vol. 53, pp. 2207-2231, 2008.

Li T et al. An efficient reconstruction method for nonuniform attenuation compensation in nonparallel beam geometries based on Novikov's explicit inversion formula. IEEE Transactions on Medical Imaging 2005; 24(10):1357-1368.

Natterer F. The mathematics of computerized tomography. Classics in Applied Mathematics. Society for Industrial and Applied Mathematics: Philadelphia, 2001, pp. 169-173.

Ciulli, E., et al., "Analytic Extrapolation Techniques and Stability Problems in Dispersion Relation Theory", Physics Reports (Section C of Physics Letters) 17, No. 4 (1975), 4 pages.

Noo F et al. Image reconstruction from truncated data in single-photon emission computed tomography with uniform attenuation. Inverse Problems 2007; 23(2):645-667.

Noo F, Clackdoyle R, Pack JD. A two-step Hilbert transform method for 2D image reconstruction. Physics in Medicine and Biology 2004; 49(17):3903-3923.

Ramachandran PA. Method of fundamental solutions: singular value decomposition analysis. Communications in Numerical Methods in Engineering 2002; 18(11):789-801.

Rullgard H. Stability of the inverse problem for the attenuated Radon transform with 180 degrees data. Inverse. Problems 2004; 20(3):781-797.

Rullgård, H, "An explicit inversion formula for the exponential Radon transform using data from 180," Research Reports in Mathematics, No. 9, 2002, 9 pages.

Tang QL et al. Exact fan-beam and 4 pi-acquisition cone-beam SPECT algorithms with uniform attenuation correction. Medical Physics 2005; 32(11):3440-3447.

Tang QL, Zeng GSL, Gullberg GT. Analytical fan-beam and cone-beam reconstruction algorithms with uniform attenuation correction for SPECT. Physics in Medicine and Biology 2005; 50(13):3153-3170.

Tretiak, O. and C. Metz, The exponential Radon-transform. SIAM Journal on Applied Mathematics, 1980. 39(2): p. 341-354.

Wang, G. and M. Jiang, Ordered-Subset Simultaneous Algebraic Reconstruction Techniques (OS-SART). J. of X-ray Science and Tech., 2004. 12(3): p. 169-177.

Wang, G., H. Yu, and Y. Ye, A scheme for multisource interior tomography. Med. Phys., 2009. 36(8): p. 3575-3581.

Yang, J.S.; H.Y. Yu, M. Jiang and G. Wang, High-order total variation minimization for interior tomography. Inverse Problems, 2010. 26(3): p. 29.

Ye et al., A General Local Reconstruction approach Based on a Truncated Hilbert Transform, Jun. 18, 2007, International Journal of Biomedical Imaging, Article ID 63634, 8 pages.

Ye YB, Yu HY, Wang G. Exact interior reconstruction with cone-beam CT. International Journal of Biomedical Imaging 2007; 2007:5, 13 pages. Article ID: 10693.

Ye YB, Zhao SY, Yu HY, Wang G. A general exact reconstruction for cone-beam CT via backprojection-filtration. IEEE Transactions on Medical Imaging 2005; 24(9):1190-1198.

Ye YB, Zhao SY, Yu HY, Wang G. Exact reconstruction for cone-beam scanning along nonstandard spirals and other curves. Developments in X-Ray Tomography IV, Proceedings of SPIE, Denver, CO, U.S.A., vol. 5535, Aug. 4-6, 2004; 293-300.

Ye, Y., Yu H.Y., and Wang G., Exact Interior Reconstruction from truncated limited-angle projection data,. International Journal of Biomedical Imaging, 2008: Article ID: 427989, 6 Pages.

Yu HY, Wang G. Studies on implementation of the Katsevich algorithm for spiral cone-beam CT. Journal of X-ray Science and Technology 2004; 12(2):97-116.

Yu, H. and G. Wang, Compressed sensing based interior tomography. Physics in Medicine and Biology 2009. 54: p. 2791-2806.

Yu, H., et al. Compressive sampling based interior reconstruction for dynamic carbon nanotube micro-CT, Journal of X-ray Science and Technology, 17(4):295-303, 2009.

Yu, H., J. Yang, et al. (2009). "Supplemental analysis on compressed sensing based interior tomography." Phys Med Biol 54(18): N425-N432.

Yu, H., Y. Ye, and G. Wang, Interior reconstruction using the truncated Hilbert transform via singular value decomposition. Journal of X-Ray Science and Technology, 2008. 16(4): p. 243-251.

Yu, H.Y.; J.S. Yang, M. Jiang and G. Wang, Interior SPECT-exact and stable ROI reconstruction from uniformly attenuated local projections. Communications in Numerical Methods in Engineering, 2009. 25(6): p. 693-710.

Zeng, G.S.L., and G.T. Gullberg, Exact emission SPECT reconstruction with truncated transmission data. Physics in Medicine and Biology, 2009. 54(11): p. 3329-3340.

Llopart, X., et al., "Medipix2: a 64-k pixel readout chip with 55 mu m square elements working in single photon counting mode.", IEEE Transactions on Nuclear Science, 2002, 49(5): 2279-2283.

* cited by examiner

A
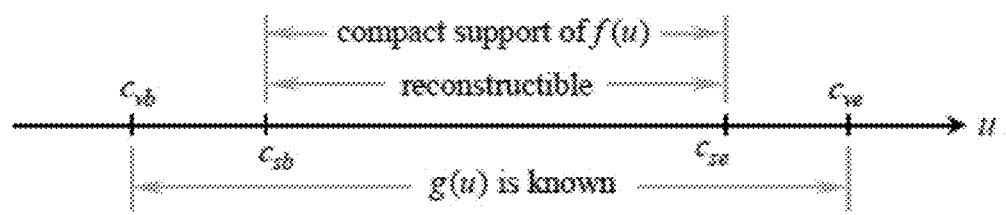
B
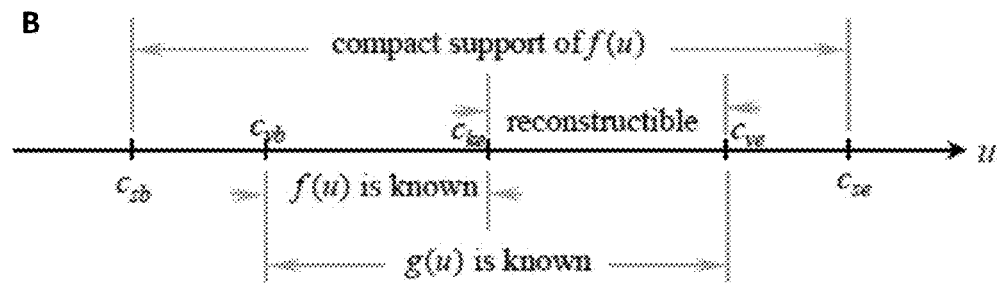
FIGS. 2A-B

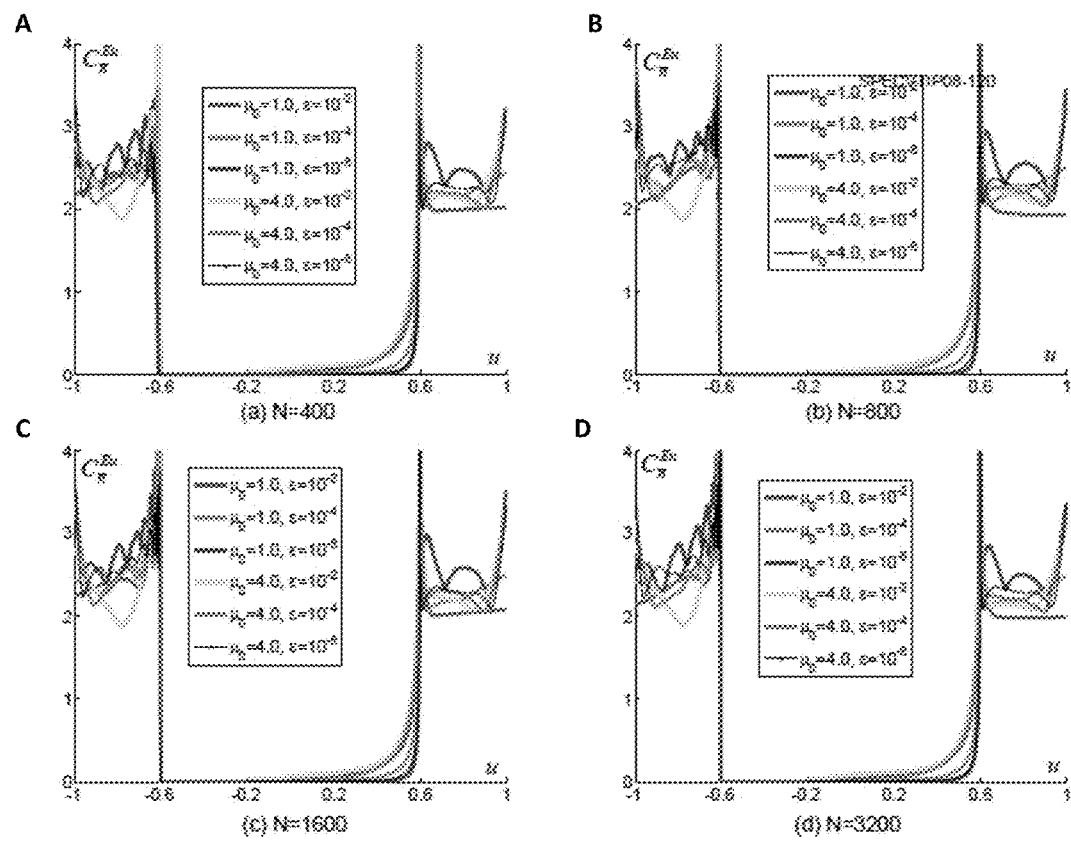
FIGS. 4A-D

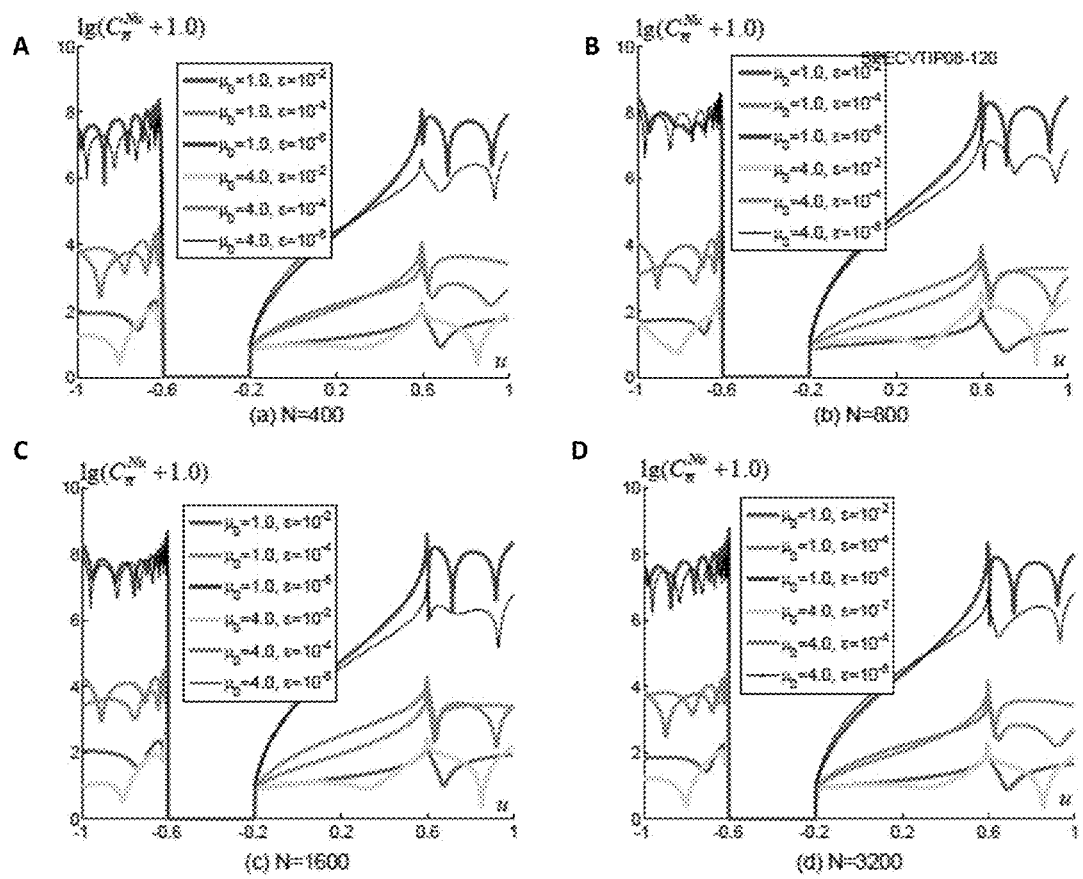
FIGS. 5A-D

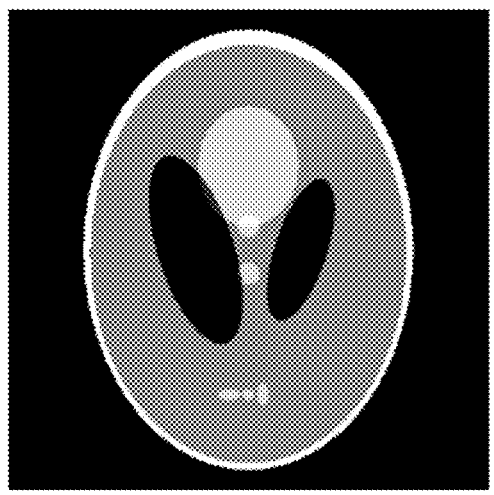 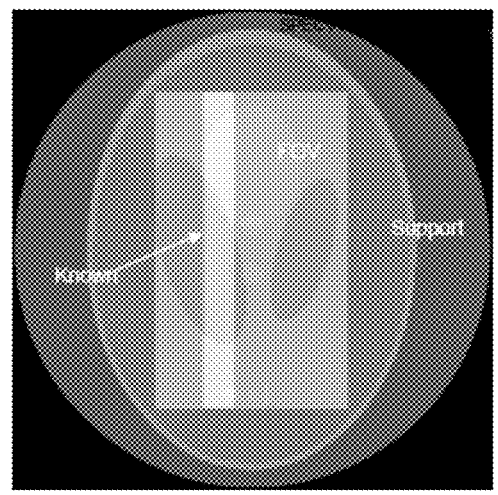
FIGS. 6A-B

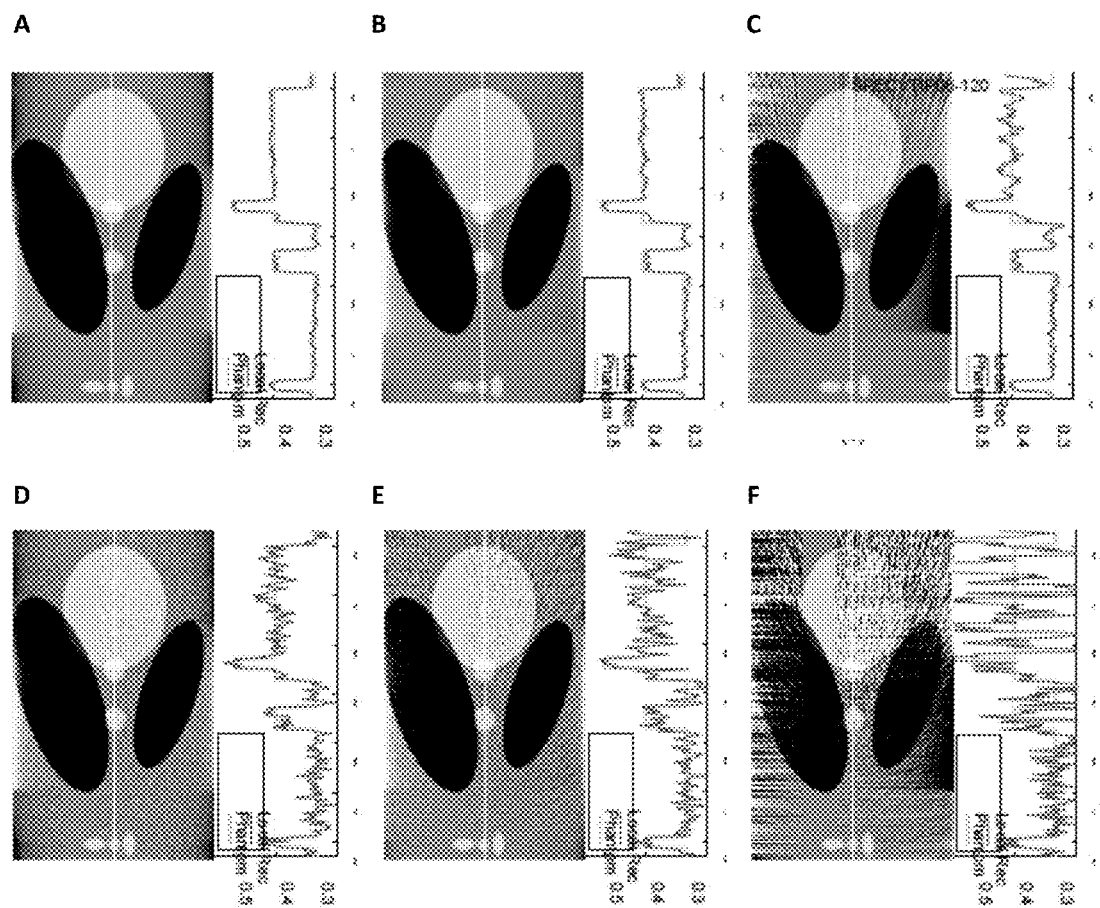
FIGS. 7A-F

A
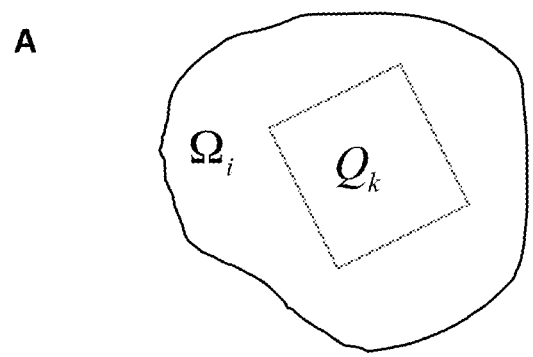
B
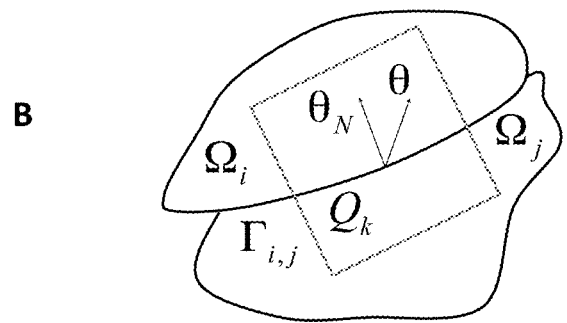
FIGS. 11A-B

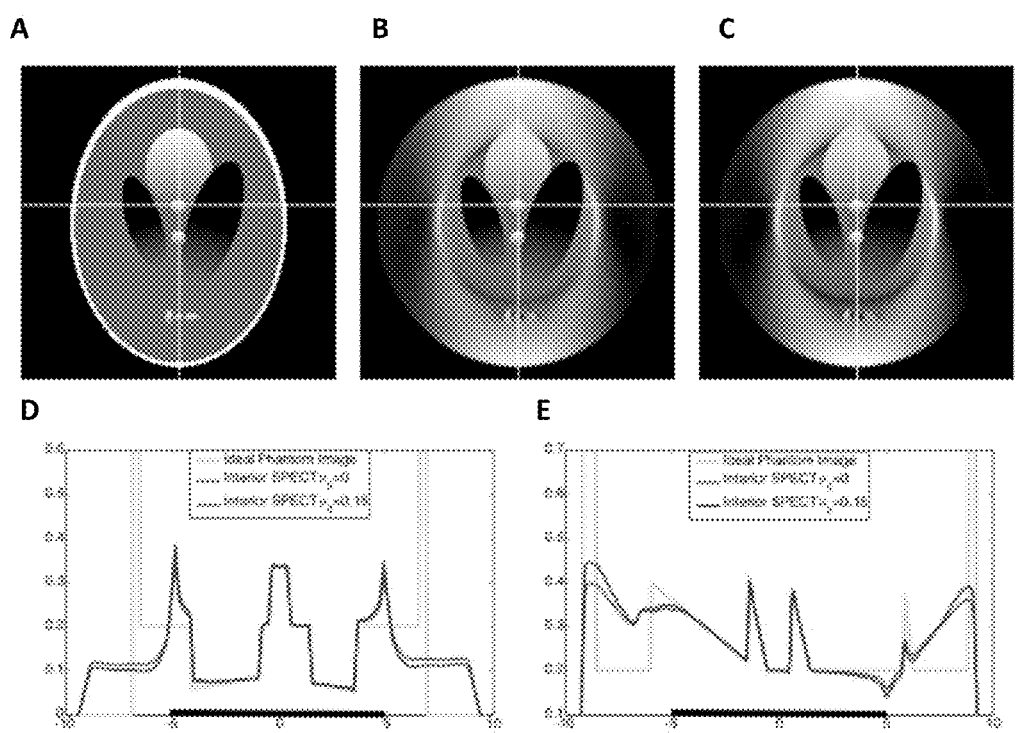
FIGS. 12A-E

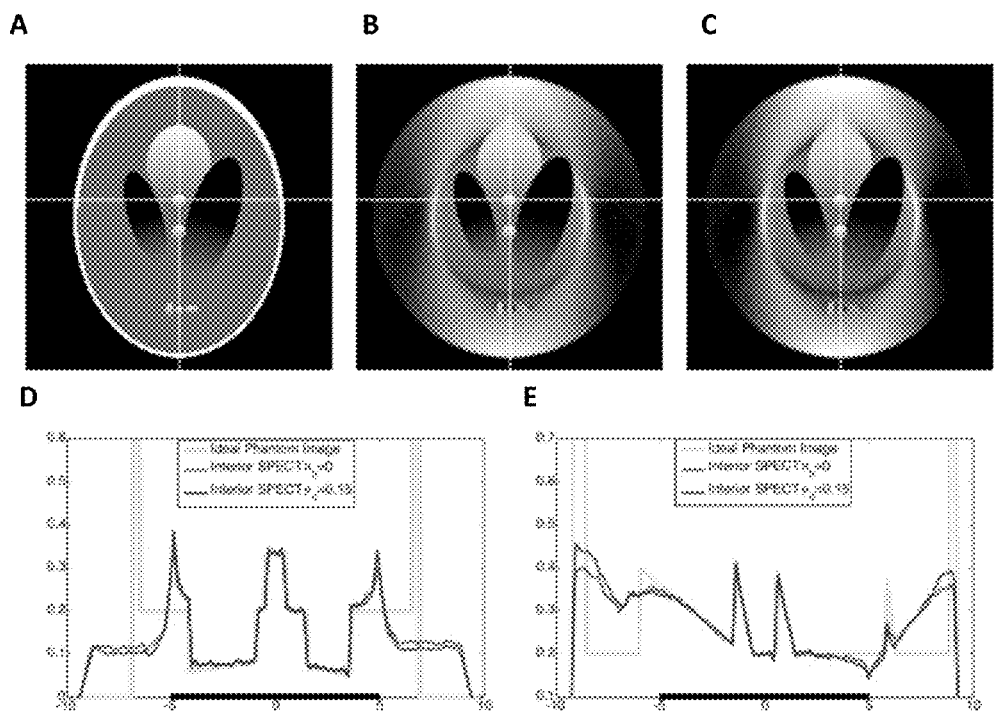
FIGS. 13A-E

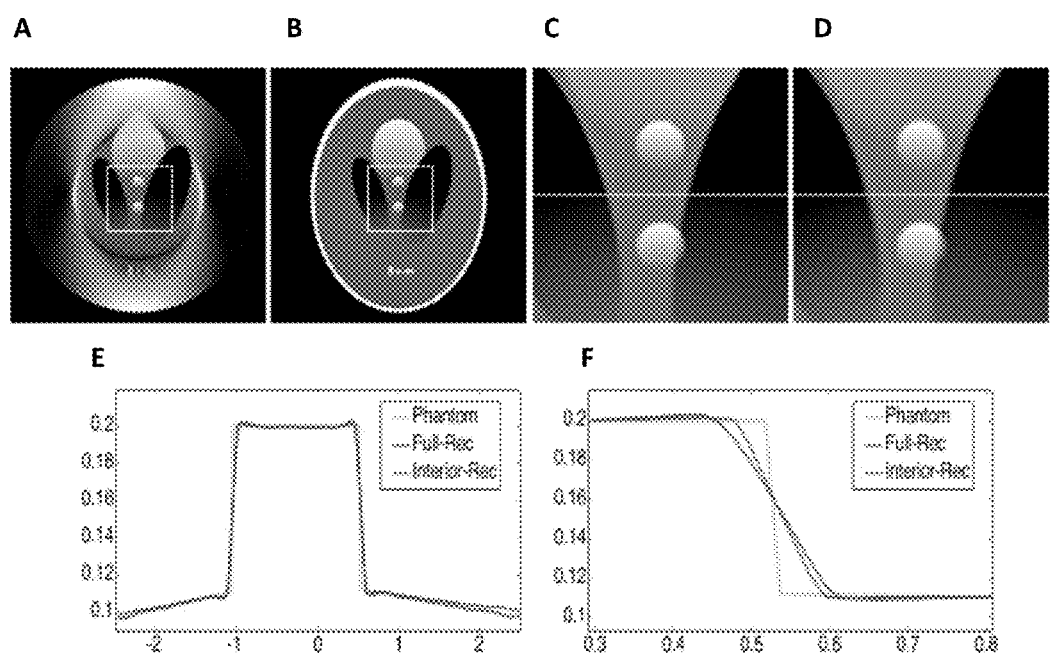
FIGS. 14A-F

METHODS FOR IMPROVED SINGLE PHOTON EMISSION COMPUTED TOMOGRAPHY USING EXACT AND STABLE REGION OF INTEREST RECONSTRUCTIONS

CROSS-REFERENCE TO RELATED APPLICATIONS

This application claims priority to and the benefit of the filing date of U.S. Provisional Application No. 61/257,443, filed Nov. 2, 2009, which is hereby incorporated by reference herein in its entirety.

STATEMENT OF GOVERNMENT INTEREST

This invention was made with government support under grants EB002667, EB004287, and EB011785 awarded by The National Institutes of Health, National Institute of Biomedical Imaging and Bioengineering. The government has certain rights in the invention.

BACKGROUND OF THE INVENTION

1. Field of the Invention

The present invention provides systems and methods for improved computed tomography (CT). More specifically, the invention provides methods for improved single photon computed tomography (SPECT) using exact and stable region of interest (ROI) reconstructions. The inventive technology can be extended across all biomedical tomography-based modalities.

2. Description of Related Art

Classic CT theory targets exact reconstruction of a whole cross-section or of an entire object from complete projections, while practical applications such as medical CT, micro- and nano-CT often need to focus on a much smaller internal region of interest (ROI). Current CT theory cannot exactly reconstruct an internal ROI only from projections associated with x-rays through the ROI because this interior problem does not have a unique solution. When applying traditional CT algorithms for interior reconstruction from projection data, features outside of the ROI may create artifacts overlapping inside features, rendering the images inaccurate or useless. Moreover, even more problems are associated with clinical imaging, as well as in the case of small animals. Although there has been an explosive growth in the development of cone-beam micro-CT scanners for such studies, the efforts are generally limited to cross-sectional or volumetric imaging at high spatial resolution of 20-100 μm and only at large radiation doses. These high radiation doses have devastating results on the patients and the animals and therefore eliminate the use of frequent CT as a possibility for medical use and pre-clinical laboratory investigations.

Facing the increasing radiation risk cause by CT examinations, a number of image reconstruction algorithms were developed to reduce the amount of necessary raw data. A recent milestone is the two-step Hilbert transform method developed by Noo et al. In their framework, an object image on a PI-line/chord can be exactly reconstructed if the intersection between the chord and the object is completely covered by the field of view (FOV). In 2006, Defrise et al. proposed an enhanced data completeness condition that the image on a chord in the FOV can be exactly reconstructed if one end of the chord segment in the object is covered by the FOV.

While the CT reconstruction algorithms are being advanced rapidly, the single photon emission computed tomography (SPECT) techniques are also experiencing remarkable improvements. As a unique biomedical tomographic imaging technique, SPECT is able to reconstruct an image from the radioactive source distribution. SPECT is performed with a gamma camera to acquire multiple 2D projections from multiple angles. Then, a tomographic reconstruction algorithm is applied to the fanbeam/cone-beam projections, yielding a 2D/3D image. Different from the line integral model for x-ray imaging, the SPECT projections can be mathematically modeled as an exponentially attenuated Radon transform. In this context, the CT reconstruction may be regarded as a special case of SPECT since all the attenuation coefficients are zeros which would allow for a better reconstruction method. However, the reconstruction techniques of CT cannot be directly used for SPECT.

Despite the impressive advancement of the CT technology, there are still unmet, critical and immediate needs such as those mentioned above for better image quality at lower radiation doses in many biomedical uses and other investigations.

SUMMARY OF THE INVENTION

The numerous limitations inherent in the scanning systems described above provide great incentive for new, better systems and methods capable of accounting for one or more of these issues. If CTs are to be seen as an accurate, reliable therapeutic answer, then improved methods for reconstructing an image should be developed that can accurately predict the image with improved temporal resolution and less artifacts at lower radiation doses.

Embodiments of the invention provide images with less than about 500 ms temporal resolution or less, such as, e.g., about 100 ms temporal resolution or less, about 80 ms or less, or about 60 ms or less, or about 50 ms or less, or about 30 ms or less, or even about 10 ms or less, and so forth. Ideally, embodiments of the invention provide methods, systems, and devices capable of reconstructing images based on scanned regions of interest with resolution than is improved as compared with such images obtained by SPECT without the algorithms of the invention. Even further preferred are methods, systems, and devices capable of achieving high quality images (e.g., same or better quality as compared with conventional SPECT-based images) with a radiation dose that is less than would be administered in a conventional SPECT-based situation.

The primary limitation to the above-mentioned, state-of-the-art treatment planning system is its need to provide good temporal resolution and image reconstruction when low doses of radiation are involved. However, as more complex applications for scanning are encountered, reconstruction of key subject areas such as the heart, lung, head and neck is cumbersome at best and may be inadequate to develop reliable diagnosis and therapies. Therefore, a more advanced system that allows for the production of better object reconstruction at lower radiation doses would be ideal. The present invention allows for the adaptation of interior SPECT to provide such improved reconstructions.

Accordingly, embodiments of the invention provide methods and systems for reconstructing an image from projection data provided by a single photon emission computed tomography scanner comprising: identifying a region of interest in an object; defining a constant attenuation coefficient and object boundary; measuring the Hilbert transform of the data through the defined region of interest; and reconstructing the image with improved temporal resolution at lower radiation doses, wherein the reconstructing comprises performing a reconstruction method that yields an exact and stable reconstruction.

In some embodiments, the reconstructed image is a portion of a heart, a lung, a head, or a neck in a patient.

In preferred embodiments, the single photon emission computed tomography projections are uniformly attenuated local projections.

In other preferred embodiments, the single photon emission computed tomography projections are modeled as a Radon transform.

In yet another embodiment, the present invention provides a method for reconstructing an image from projection data provided by a single photon emission computed tomography scanner comprising: identifying a region of interest in an object; defining the region of interest as piecewise polynomial; measuring the Hilbert transform of the data through the defined region of interest; and reconstructing the image with improved temporal resolution at lower radiation doses, wherein the reconstructing comprises performing an improved high order TV minimization.

In such embodiments, the improved high order TV minimization has an explicit formula for cases with polynomial order of about 2 or more.

The features and advantages of embodiments of the present invention will be apparent to those skilled in the art. While numerous changes may be made by those skilled in the art, such changes are within the spirit of the invention.

Specific embodiments include a computed tomography-based reconstruction method comprising reconstructing a region of interest (ROI) of an object into an image from single photon emission computed tomography (SPECT) projection data of the ROI by modeling the projection data as an attenuated Radon transform comprising formula:

$$P_o(\theta, s) = \int_{-\infty}^{\infty} f(s\theta + t\theta^\perp) e^{-\int_t^\infty \mu(s\theta + \tilde{t}\theta^\perp) d\tilde{t}} dt$$

where subscript "o" indicates original projection data, $\theta=(\cos\theta, \sin(\theta))$, $\theta^\perp=(-\sin\theta, \cos(\theta))$, and $\mu(x)$ is the attenuation coefficient map on the whole compact support $\Omega$.

Such methods can further comprise: defining a constant attenuation coefficient and object boundary; and measuring the Hilbert transform of the data through the ROI. Even further, methods according to embodiments of the invention can further comprise: defining the region of interest as piecewise polynomial; and reconstructing the image by performing a high order TV minimization.

Other embodiments of the invention include a method further comprising scanning an object using a SPECT scanner to acquire projection data relating to the object. Methods can also include single photon emission computed tomography projection data which are uniformly attenuated local projections. Further, the projection data $P_o(\theta,s)$ can be acquired with gamma camera. According to method embodiments, the reconstruction image can be reconstructed using guided computed tomography and/or nano-computer tomography.

Also included within the scope of the invention is a SPECT system comprising: a SPECT scanner operably configured for scanning an object to acquire projection data relating to the object; a processing module operably configured for reconstructing the scanned portion of the object into an image by identifying a region of interest (ROI), measuring the Hilbert transform of the data through the defined ROI, performing a reconstruction method that yields an exact and stable reconstruction; and a processor for executing the processing module.

Such systems can be operably configured for scanning and reconstructing a heart, lung, head, or neck of a subject. Even further, such systems can be operably configured such that the reconstructing employs singular value decomposition.

Systems of the invention can be operably configured, wherein the single photon emission computed tomography projection data are uniformly attenuated local projections.

Preferred system embodiments of the invention are operably configured such that the processing module is capable of modeling the projection data as an attenuated Radon transform comprising formula:

$$P_o(\theta, s) = \int_{-\infty}^{\infty} f(s\theta + t\theta^\perp) e^{-\int_t^\infty \mu(s\theta + \tilde{t}\theta^\perp) d\tilde{t}} dt$$

where subscript "o" indicates original projection data, $\theta=(\cos\theta, \sin(\theta))$, $\theta^\perp=(-\sin\theta, \cos(\theta))$, and $\mu(x)$ is the attenuation coefficient map on the whole compact support $\Omega$.

Projection data $P_o(\theta,s)$ can be acquired with a gamma camera according to some embodiments of the present invention.

Even further, systems of the invention can be operably configured for reconstructing the image using guided computed tomography and/or nano-computer tomography.

It is noted that although only specific embodiments or methods, systems, and devices are listed in this summary, these embodiments can be expanded to cover methods, systems, and/or devices regardless of the type of embodiment is listed. For example, when referring to only a method, such disclosure should be construed to include devices and systems comprising the same elements. Further, these specific embodiments can be altered or modified by omitting one or more elements specifically listed and/or by combining elements of another listed embodiment therewith. For example, if a method embodiment refers to having two method steps, that embodiment can be construed as a system capable of performing only one of those functions and/or as a system capable of performing both of the listed functions and any other function listed for another embodiment. It is within the capabilities of those of ordinary skill in the art to modify this disclosure in this way.

In the context of this disclosure, accuracy or theoretically exact means that the algorithm is theoretically exact for a good portion of voxels in the object or theoretically exact if a practically insignificant portion of data could be handled in a more complicated fashion.

BRIEF DESCRIPTION OF THE DRAWINGS

These drawings illustrate certain aspects of some of the embodiments of the present invention, and should not be used to limit or define the invention.

FIG. 2A is a schematic diagram of various exact reconstruction conditions based on the generalized Hilbert transform using the exact reconstruction region by Noo et al.

FIG. 2B is a schematic diagram of various exact reconstruction conditions based on the generalized Hilbert transform using the exact reconstruction region described by the methods of this application.

FIG. 4 is a graphic representation allowing for the visualization of the exactness measurement $C_{\bar{n}}^{Nu}$ for different configurations of N, $\mu_o$ and $\epsilon$.

FIG. 5 is a graphic representation allowing for the visualization of the stability measurement $C_{\bar{n}}^{Nu}$ for different configurations of N, $\mu_o$ and $\epsilon$.

FIG. 6A is an illustration of the Shepp-Logan phantom for interior reconstruction of SPECT in a display window [0.15, 0.45].

FIG. 6B is an illustration of the Shepp-Logan phantom for interior reconstruction of SPECT with a disk support, a rectangular field of view and a strip-shaped known prior region.

FIG. 7 is an illustration of the SPECT interior reconstruction results. The left, middle and right columns are respectively for the case=0 cm$^{-1}$, 0.15 cm$^{-1}$ and 0.30 cm$^{-1}$. The top row images are reconstructed from noise-free projection data, while the bottom row of images are reconstructed from noisy-data with 1.0% Gaussian white noise. For each image, profile along the central white line is attached on the right. The display window is [0.15,0.45].

FIG. 11 is a schematic illustrating the $Q_k$ of (a) the first and (b) second types.

FIG. 12A is an illustration of the interior SPECT reconstruction of the Shepp-Logan phantom modified with linear variations over sub-domains from the original phantom. The display window is [0.1,0.4].

FIGS. 12B and C are illustrations of the interior SPECT reconstruction of the Shepp-Logan phantom modified with linear variations over sub-domains using the inventive HOT minimization based algorithm after 40 iterations with the attenuation coefficient $\mu_o$=0 and $\mu_o$=0.15, respectively. The display window is [0.1,0.4].

FIG. 12D is an illustration of representative profiles along the white horizontal lines. The horizontal axis represents the 1D coordinate, the vertical axis denotes the functional value, and the black thick lines on the horizontal axis indicates the ROI.

FIG. 12E is an illustration of representative profiles along the white vertical lines. The horizontal axis represents the 1D coordinate, the vertical axis denotes the functional value, and the black thick lines on the horizontal axis indicates the ROI.

FIG. 13A is an illustration of the interior SPECT reconstruction of the Shepp-Logan phantom modified with linear variations over sub-domains from the original phantom with 1% Gaussian noise in the measured data. The display window is [0.1,0.4].

FIGS. 13B and C are illustrations of the interior SPECT reconstruction of the Shepp-Logan phantom modified with linear variations over sub-domains using the inventive HOT minimization based algorithm after 40 iterations with the attenuation coefficient $\mu_o$=0 and $\mu_o$=0.15, respectively with 1% Gaussian noise in the measured data. Display window is [0.1,0.4].

FIG. 13D is an illustration of representative profiles along the white horizontal lines with 1% Gaussian noise in the measured data. The horizontal axis represents the 1D coordinate, the vertical axis denotes the functional value, and the black thick lines on the horizontal axis indicates the ROI.

FIG. 13E is an illustration of representative profiles along the white vertical liner with 1% Gaussian noise in the measured data. The horizontal axis represents the 1D coordinate, the vertical axis denotes the functional value, and the black thick lines on the horizontal axis indicates the ROI.

FIG. 14A is an illustration demonstrating the spatial resolution improvement with interior SPECT with a high-resolution interior reconstruction in a 1024×1024 matrix using the same projection dataset and parameters as that for FIG. 12C.

FIG. 14B is an illustration demonstrating the spatial resolution improvement with interior SPECT using the counterpart of 14A with the same detector elements covering the whole object.

FIGS. 14C and D are illustrations showing the magnifications of the ROI in FIGS. 14A and B, respectively.

FIG. 14E is an illustration of the profiles along the while lines in FIGS. 14 C and D, respectively.

FIG. 14F is an illustration of the magnification of a portion of FIG. 14E demonstrating the special resolution improvement with the interior SPECT approach.

DETAILED DESCRIPTION OF VARIOUS EMBODIMENTS OF THE INVENTION

SPECT is an important biomedical imaging modality. However, since gamma cameras are expensive and bulky, truncated projection data are either preferred or unavoidable. Inspired by the recent results on interior tomography in the x-ray CT field, the present invention describes an interior SPECT approach for exact and stable reconstruction of a region of interest (ROI) from uniformly attenuated local projection data. In certain embodiments, the reconstruction is aided by prior knowledge of a sub-region in the ROI. The present invention provides exact and stable interior SPECT systems, methods, and devices.

In accordance with embodiments of the present invention, a method of the present invention may comprise introducing analytic continuation of the algorithms for use with conventional CT technologies in order to obtain better reconstruction images in SPECT. One of the many potential advantages of the methods of the present invention, only some of which are discussed herein, is that images with less blurring and improved temporal resolution may be obtained even when there is much lower radiation exposure in the object being scanned, when compared with conventional radiation doses.

The current invention may provide benefits to various types of interior tomography including, but not limited to, cardiac, lung, head (e.g., dental) neck tomography, guided-CT procedures, and nano-CT. In the medical field and in biomedical science, the methods disclosed herein may greatly reduce the amount of radiation necessary to obtain a good image and thereby potentially allow increased early detection of diseases, reduced exposure to radioactivity in patients, and/or reduced costs associated with CTs. Better temporal resolution at low radiation doses in the images may provide a cost savings by reducing the number of images needed to conclude a finding. This type of scanning may likewise provide more flexibility in designing experiments in small animals in order to better study these diseases and develop effective treatments.

Another potential advantage is the use of an improved high order TV minimization to better reconstruct an image at lower radiation doses through interior SPECT without a defined object boundary. In such embodiments, the ROI is assumed to be piecewise polynomial. There are at least two more advantages associated with interior SPECT. First of all, the size of a SPECT camera can be accordingly reduced, substantially lowering the system cost. This is especially desirable when an expensive high-resolution camera is needed or a low-cost system is intended for wider healthcare coverage. Use of a smaller field of view would also allow the camera to be closer to a subject under study, improving the signal-to-noise ratio.

SPECT Interior Reconstruction Summary.

Figure 1:
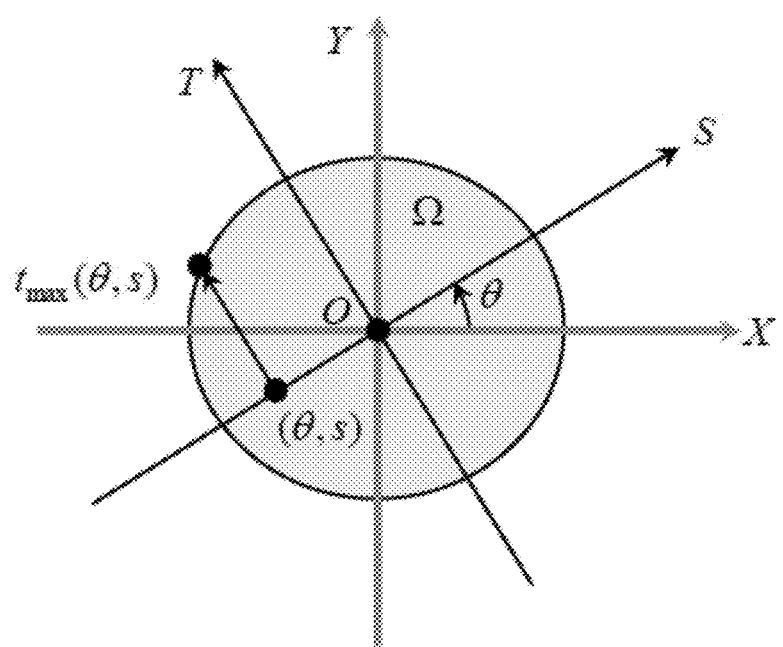
FIG. 1 is a schematic diagram showing a parallel beam coordinate system for SPECT imaging.

The results from the SPECT interior reconstruction are summarized herein. In certain embodiments, the constant attenuation coefficient and the object boundaries are known. In other embodiments discussed in detail below, the object boundaries are not known. In embodiments where the constant attenuation coefficient and the object boundaries are known, $f(x)$ may be a 2D smooth distribution function defined on a convex compact support $\Omega$ with $x=(x,y)\in\Omega$. Mathematically, in a parallel-beam geometry (FIG. 1), the SPECT projections of $f(x)$ can be modeled as the attenuated Radon transform seen in EQUATION 1:

$$P_o(\theta, s) = \int_{-\infty}^{\infty} f(s\theta + t\theta^\perp) e^{-\int_t^\infty \mu(s\theta + \tilde{t}\theta^\perp) d\tilde{t}} dt, \quad \text{EQUATION 1}$$

where the subscript "o" indicates original projection data, $\theta=(\cos\theta, \sin(\theta))$, $\theta^\perp=(-\sin\theta, \cos(\theta))$, and $\mu(x)$ is the attenuation coefficient map on the whole compact support $\Omega$. For practical applications $P_o(\theta,s)$ can be acquired by a gamma camera. For most imaging subjects such as the brain, the attenuation map can be approximated as a uniform distribution:

$$\mu(x) = \begin{cases} \mu_0 & x \in \Omega \\ 0 & x \notin \Omega \end{cases}, \quad \text{EQUATION 2}$$

where $\mu_0$ is a constant. Since the object function is compactly supported, the maximum coordinate along the direction $\theta^\perp$ of the intersection between support $\Omega$ and the integralline of the projection $P_0(\theta,s)$ can be determined. Without loss of generality, and without wishing to be limited by theory, the coordinate is denoted as $t_{max}(\theta,s)$ and EQUATION 1 becomes EQ. 3:

$$P_o(\theta, s) = e^{-\mu_0 t_{max}(\theta,t)} \int_{-\infty}^{\infty} f(s\theta + t\theta^\perp) e^{\mu_0 t} dt.$$

For certain embodiments, we can assume that the convex compact support $\Omega$ and the constant attenuation coefficient $\mu_o$ are known. Once the coordinate system is chosen, we can determine $t_{max}(\theta,s)$ for all the whole projection dataset. By multiplying a weighting factor $e^{\mu_0 t_{max}(\theta,s)}$, the projection model of SPECT can be reduced to EQUATION 4:

$$P_w(\theta, s) = P_o(\theta, s) e^{\mu_0 t_{max}(\theta,s)} = \int_{-\infty}^{\infty} f(s\theta + t\theta^\perp) e^{\mu_0 t} dt, \quad \text{EQUATION 4}$$

where the subscript "w" indicates that the weighted projection data. A weighted backprojection of the differential projection data may be denoted by EQUATION 5:

$$g(x) = \int_0^\pi e^{-\mu_0 x \cdot \theta^\perp} \frac{\partial P_w(\theta, s)}{\partial s}\bigg|_{s=x\cdot\theta} d\theta. \quad \text{EQUATION 5}$$

In 2004, Rullgard proved a relationship linking the object image $f(x)$ and the weighted backprojection $g(x)$ as $$g(x) = -2\pi PV \int_{-\infty}^{+\infty} ch_{\mu_0}(y - \tilde{y}) f(x, \tilde{y}) d\tilde{y}, \quad \text{EQUATION 6}$$

where "PV" represents the Cauchy principle value integral, and $ch_{\mu_0}$ may be defined by EQUATION 7:

$$ch_{\mu_0}(y) = \frac{\cosh(\mu_0 y)}{\pi y} = \frac{e^{\mu_0 y} + e^{-\mu_0 y}}{2\pi y}. \quad \text{EQUATION 7}$$

When $\mu_0 \to 0$, $ch_{\mu_0}$ becomes the Hilbert transform kernel may be in consistence with the results in the CT field. EQUATION 6 depicts a generalized Hilbert transform, and the corresponding Hilbert filtering line a generalized PI-line. The backprojection operation for $g(x)$ in EQUATION 5 may only involve local projection data whose integral paths intersect with the point x. Hence, inside a field of view (FOV) or region-of-interest (ROI) any point may be irradiated at least from an angular range of 180 degrees, and its backprojection $g(x)$ of differential data can be exactly computed.

Without loss of generality, or wishing to be limited by theory, let us denote a 2D $f(x)$ on a PI-line/chord as $f(u)$ and the backprojection $g(x)$ as $g(u)$, where u is a 1D coordinate along the PI-line.

The intersection of the convex compact support $\Omega$ and the PI-line as the interval $(c_{sb}, c_{se})$ with $c_{sb} < c_{se}$, which implies that $f(u)=0$ for $u \notin (c_{sb}, c_{se})$ where the subscripts "sb" and "se" represent the starting and ending points of the support may be denoted. Also, the intersection of the FOV and PI-line as an interval $(c_{vb}, c_{ve})$ with $c_{vb} < c_{ve}$ where the subscripts "vb" and "ve" represent starting and ending points of the FOV may be denoted. Using the above notations, EQUATION 6 can be reduced as:

$$g(u) = -2\pi PV \int_{c_{sb}}^{c_{se}} ch_{\mu_0}(u - \tilde{u}) f(\tilde{u}) d\tilde{u} \quad u \in (c_{vb}, c_{ve}). \quad \text{EQUATION 8}$$

In 2007, Noo et al. extended their two-step Hilbert CT method to the case of SPECT, and showed that an object image $f(u)$ can be exactly reconstructed on the whole compact support interval $(c_{sb}, c_{se})$ if $c_{vb} < c_{sb} < c_{se} < c_{ve}$ (FIG. 2A). The present invention further extend this result for SPECT in the case $c_{sb} < c_{vb} < c_{ve} < c_{se}$. In some embodiments, a real number $c_{ke}$ may exist and may satisfy $c_{sb} < c_{vb} < c_{ve} < c_{se}$ with $f(u)$ being known on the interval $(c_{vb}, c_{ke})$. In certain embodiments, the present invention shows that $f(u)$ can be exactly and stably reconstructed, as shown in FIG. 2B, where the subscript "ke" represents the ending point of the known part. The main results can be summarized as:

Theorem 1:

Assume that $c_{sb} < c_{vb} < c_{ve} < c_{se}$ and a smooth function $f(u)$ is supported on $(c_{sb}, c_{se})$. The function $f(u)$ can be exactly reconstructed on $(c_{vb}, c_{ve})$ if (i) $f(u)$ is known on $(c_{vb}, c_{ke})$, (ii) $g(u)$ is known on $(c_{vb}, c_{ve})$, and (iii) the constant $\mu_0$ and $m_{\mu_0}$ are known, where:

$$m_{\mu_0} = \int_{c_{sb}}^{c_{se}} f(\tilde{u})\cosh(\mu_0 \tilde{u})d\tilde{u}. \qquad \text{EQ. 9}$$

In certain embodiments, the parameter $c_{kb}=c_{vb}$ in the above theorem were omitted, and in practical applications $m_{\mu 0}$ could be directly computed from the projection datum along the path through the corresponding PI-line. In such embodiments, it can be assumed that the known $f(u)$ are on any subinterval of the line-segment $(c_{vb}, c_{ve})$ or a union of such intervals. The corresponding results can be directly obtained by applying Theorem 2.1 repeatedly.

Uniqueness Analysis.

Without loss of generality or wishing to be limited by theory, we assume $c_{sb}=-1$ and $c_{se}=1$. In other embodiment, we can arrive at this standardization by a linear coordinate transform. For the case $c_{vb}<-1$ and $1<c_{ve}$, Noo et al. reduced the reconstruction issue to a Fredholm integral equation of the second kind for $h(u)$ on the interval $[-1,1]$:

$$h(u) = h_d(u) + \frac{1}{\pi} m_{\mu_0} + Kh, \qquad \text{EQ 10}$$

$$h(u) = f(u)\sqrt{1-u^2}, \qquad \text{EQ 11}$$

$$h_d(u) = -PV\int_{-1}^{1} \frac{\sqrt{1-\tilde{u}^2}}{\pi(u-\tilde{u})} g(\tilde{u})d\tilde{u}, \qquad \text{EQ 12}$$

$$(Kh)(u) = \int_{-1}^{1} \frac{h(\tilde{u})}{\sqrt{1-\tilde{u}^2}} \overline{k}_{\mu_0}(u,\tilde{u})d\tilde{u}, \qquad \text{EQ 13}$$

with $$\overline{k}_{\mu_0}(u,\tilde{u}) = \mu_0 PV\int_{-1}^{1} \frac{\sqrt{1-v^2}}{\pi(u-v)} \eta(\mu_0(v-\tilde{u}))dv + \frac{1}{\pi}(1-\cosh\mu_0\tilde{u}), \qquad \text{EQ 14}$$

$$\eta(u) = \begin{cases} (\cosh u - 1)/(\pi u) & u \neq 0 \\ 0 & u = 0 \end{cases}. \qquad \text{EQ 15}$$

Noo et al. proved that the Cauchy principle value integral in EQUATION 14 can be removed because EQUATION 15 is a smooth function, leading to that $\overline{k}_{\mu_0}(u,\tilde{u})$ is a smooth and continuous function over the region $(u,\tilde{u})\in[-1,1]\times[-1,1]$. Using the following identical equation $$PV\int_{-1}^{1} \frac{\sqrt{1-v^2}}{\pi(u-v)} dv = u, |u| \leq 1, \qquad \text{EQ 16}$$

$\overline{k}_{\mu_0}(u,\tilde{u})$ can be rewritten as EQUATION 17:

$$\overline{k}_{\mu_0}(u,\tilde{u}) = \mu_0 PV\int_{-1}^{1} \sqrt{1-v^2}\, \overline{\eta}(u,v,\tilde{u})dv + \mu_0 u \eta(\mu_0(u-\tilde{u})) + \frac{1}{\pi}(1-\cosh\mu_0\tilde{u}),$$

where $$\overline{\eta}(u,v,\tilde{u}) = \frac{\eta(\mu_0(v-\tilde{u})) - \eta(\mu_0(u-\tilde{u}))}{\pi(u-v)}. \qquad \text{EQUATION 18}$$

Note that both $\overline{\eta}(u,v,\tilde{u})$ and $\eta(\mu_0(u-\tilde{u}))$ are analytical with respect to the variable $u$, and $\overline{k}_{\mu_0}(u,\tilde{u})$ is analytical with respect to the variable $u$. Hence, $(Kh)(u)$ can be analytically extended to the whole complex plane.

When the case $-1=c_{sb}<c_{vb}<c_{ve}<c_{se}$ is considered, EQUATION 10 can be rewritten as EQ. 19:

$$h(u)=h_1(u)+h_2(u),$$

where $$h_1(u) = -PV\int_{c_{vb}}^{c_{ve}} \frac{\sqrt{1-\tilde{u}^2}}{\pi(u-\tilde{u})} g(\tilde{u})d\tilde{u} + \frac{1}{\pi} m_{\mu_0}, \qquad \text{EQ. 20}$$

$$h_2(u) = -PV\left(\int_{-1}^{c_{vb}} + \int_{c_{ve}}^{1}\right)\left(\frac{\sqrt{1-\tilde{u}^2}}{\pi(u-\tilde{u})} g(\tilde{u})d\tilde{u}\right) + Kh(u), \qquad \text{EQ. 21}$$

By our assumption in Theorem 1 of the present invention, $h_1(u)$ is known for $u \in R$ and $h(u)$ is known on the interval $(c_{vb}, c_{ke})$, we obtain that $$h_2(u)=h(u)-h_1(u) \qquad \text{EQ. 22}$$

can be known on the interval $(c_{vb}, c_{ke})$. Because the principal integral of the first term of Eq. (21) is defined on $(-1, c_{vb}) \cup (c_{ve}, 1)$, $h_2(u)$ is analytic on the interval $(c_{vb}, c_{ve})$, and it can be analytically extended to the complex plane [ ] with cuts along the real axis from $-\infty$ to $c_{vb}$ and from $c_{ve}$ to $+\infty$. Therefore, $h_2(u)$ can be determined on the interval $(c_{vb}, c_{ve})$ by its value on the interval $(c_{vb}, c_{ke})$. As a result, $h(u)$ (or $f(u)$) can be uniquely reconstructed on the interval $(c_{vb}, c_{ve})$.

In some embodiments, a stability analysis can be performed for our Theorem 1 as follows. In practice, we have the measurement $g_r(u)$ of $g(u)$ and reconstruct $f_r(u)$ from $g_r(u)$. Assume that these functions satisfy the following conditions:

$|h(u)-h_r(u)|\leq \epsilon$ for $u \in (c_{vb}, c_{ke})$ ($f(u)$ is known in $(c_{vb}, c_{ke})$); \hfill (i)

$|(h_r)_1(u)-h_1(u)|\leq \epsilon$ for $u \in (c_{vb}, c_{ve})$; \hfill (ii)

$$|f(u)| \le \frac{M_1}{2}, |f_r(u)| \le \frac{M_1}{2}, \text{ for } u \in (-1, 1); \quad \text{(iii)}$$

$$\frac{1}{\pi}\sqrt{1-u^2}\,|Hf(u)| \le \frac{M_2}{2}, \frac{1}{\pi}\sqrt{1-u^2}\,|Hf_r(u)| \le \frac{M_2}{2}, \quad \text{(iv)}$$
$$\text{for } u \in (-1, c_{vb}) \cup (c_{ve}, 1);$$

$$m_{\mu_0} = \int_{-1}^{1} f(\tilde{u})\cosh(\mu_0 \tilde{u})d\tilde{u} = \int_{-1}^{1} f_y(\tilde{u})\cosh(\mu_0 \tilde{u})d\tilde{u}\,(m_{\mu_0}\text{ is known}) \quad \text{(v)}$$

The above conditions lead to $$|h_{err}(u)| \le \epsilon \text{ for } u \in (c_{vb}, c_{ke}); \quad \text{(i)}$$

$$|h_{1,err}(u))| \le \epsilon \text{ for } u \in (c_{vb}, c_{ve}); \quad \text{(ii)}$$

$$|f_{err}(u)| \le M_1 \text{ for } u \in (-1,1); \quad \text{(iii)}$$

$$\frac{1}{\pi}\sqrt{1-u^2}\,|Hf_{err}(u)| \le M_2 \text{ for } u \in (-1, c_{vb}) \cup (v_{ve}, 1); \quad \text{(iv)}$$

Where, EQUATION 23:

$$h_{err}(u)=h_r(u)-h(u), h_{1,err}(u)=(h_r)_1(u)-h_1(u), f_{err}(u)=f_r(u)-f(u).$$

Similarly, the present invention denotes $$h_{2,err}(u)=(h_r)_2(u)-h_2(u). \quad \text{EQUATION 24}$$

By choosing two arbitrary constants $\tilde{c}_{vb}, \tilde{c}_{ve}$ such that $c_{vb} < \tilde{c}_{vb} < c_{ke} < \tilde{c}_{ve} < c_{ve}$. On the interval $(\tilde{c}_{vb}, \tilde{c}_{ve})$, it is possible to have:

$$h_{err}(u)=h_{1,err}(u)+h_{2,err}(u). \quad \text{EQUATION 25}$$

Especially, on the interval $(\tilde{c}_{vb}, c_{ke})$, it is possible to have $$|h_{2,err}(u)| \le |h_{1,err}(u)|+|h_{err}(u)| \le 2\epsilon. \quad \text{EQ. 26}$$

In order to obtain a upper bound of $|h_{2,err}(u)|$ on the interval $(c_{ke}, \tilde{c}_{ve})$, the present invention uses Nevanlinna's principle.

Lemma (Nevanlinna's Principle).

Let $\Omega \subset \mathbb{C}$ be a domain and D be a segment of the boundary $\partial \Omega$. If $f(z)$ is an analytical function in $\Omega$ such that $$|f(z)| \le \begin{cases} \epsilon & \text{for } z \in D \\ M & \text{for } z \in \partial \Omega \backslash D \end{cases}$$

and $\omega(z)$ is a harmonic function in $\Omega$ such that $$\omega(z) = \begin{cases} 0 & \text{for } z \in D \\ 1 & \text{for } z \in \partial \Omega \backslash D, \end{cases}$$

then $|f(z)| \le M^{\omega(z)}\epsilon^{1-\omega(z)}$

Figure 3:
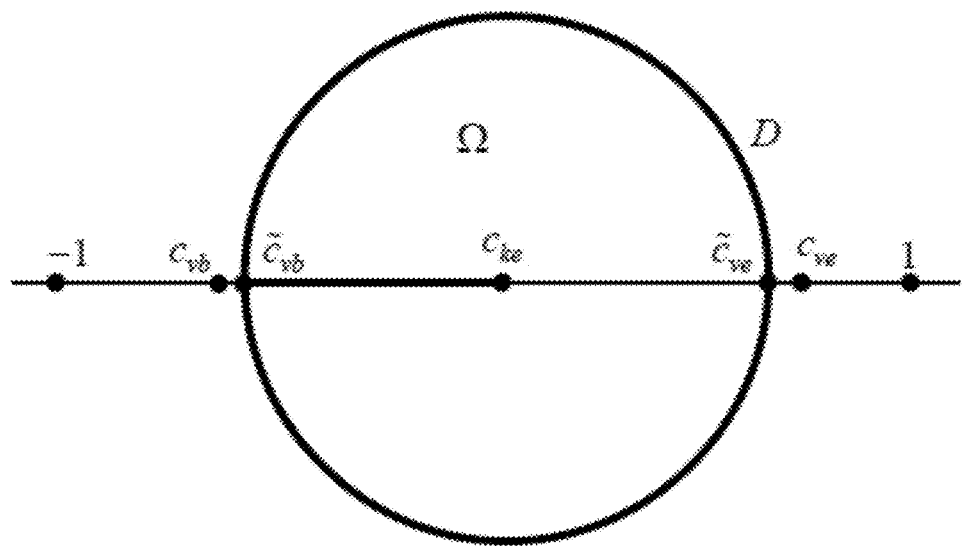
FIG. 3 is a schematic diagram of the interior reconstruction configuration in terms of Nevanlinna principle.

Let B to be the disk with diameter $(\tilde{c}_{vb}, \tilde{c}_{ve})$, $\Omega = B \backslash (\tilde{c}_{vb}, c_{ke})$, then $\partial \Omega = D + \partial B$, where $D = (\tilde{c}_{vb}, c_{ke})$, and $\partial B$ is the circle with diameter $(\tilde{c}_{vb}, \tilde{c}_{ve})$ (FIG. 3). Recall that $$h_{2,err}(u) = \quad \text{EQUATION 27}$$
$$-PV\left(\int_{-1}^{c_{vb}} + \int_{c_{ve}}^{1}\right)\left(\frac{\sqrt{1-\tilde{u}^2}}{\pi(u-\tilde{u})}Hf_{err}(\tilde{u})\right)d\tilde{u} + Kh_{err}(u)$$

For $z \in \partial B$, $$|h_{2,err}(z)| \le \quad \text{EQ. 28}$$
$$\left|\left(\int_{-1}^{c_{vb}} + \int_{c_{ve}}^{1}\right)\left(\frac{\sqrt{1-\tilde{u}^2}}{\pi(z-\tilde{u})}Hf_{err}(\tilde{u})\right)d\tilde{u}\right| + |Kh_{err}(z)|,$$

Where $$\left|\left(\int_{-1}^{c_{vb}} + \int_{c_{ve}}^{1}\right)\left(\frac{\sqrt{1-\tilde{u}^2}}{\pi(z-\tilde{u})}Hf_{err}(\tilde{u})\right)du\right| \le \quad \text{EQUATION 29}$$

$$\int_{-1}^{c_{vb}} \frac{\left|\sqrt{1-\tilde{u}^2}\,Hf_{err}(\tilde{u})\right|}{\pi(\text{Re}z - \tilde{u})}d\tilde{u} +$$

$$\int_{c_{ve}}^{1} \frac{\left|\sqrt{1-\tilde{u}^2}\,Hf_{err}(\tilde{u})\right|}{\pi(\tilde{u} - \text{Re}z)}d\tilde{u} \le$$

$$\int_{-1}^{c_{vb}} \frac{M_2}{\text{Re}z - \tilde{u}}d\tilde{u} + \int_{c_{ve}}^{1} \frac{M_2}{u - \text{Re}z}d\tilde{u} =$$

$$M_2\left(\ln\left(\frac{\text{Re}z+1}{\text{Re}z - c_{vb}}\right) + \ln\left(\frac{1-\text{Re}z}{c_{ve}-\text{Re}z}\right)\right) \le$$

$$M_2\left(\ln\left(\frac{\tilde{c}_{vb}+1}{\tilde{c}_{vb} - c_{vb}}\right) + \ln\left(\frac{1-\tilde{c}_{ve}}{c_{ve}-\tilde{c}_{ve}}\right)\right),$$

and $$|Kh_{err}(z)| \le \left|\int_{-1}^{1} f_{err}(\tilde{u})\bar{k}_{\mu_0}(z, \tilde{u})d\tilde{u}\right| \le CM_1,$$

with $$C = \max_{|z|\le 1, |\tilde{u}|\le 1} |\bar{k}_{\mu_0}(z, \tilde{u})|. \quad \text{EQ 30}$$

The present invention concludes that (i) $\quad$ EQ. 31

$$|h_{2,err}(z)| \le M_2\left(\ln\left(\frac{\tilde{c}_{vb}+1}{\tilde{c}_{vb}-c_{vb}}\right) + \ln\left(\frac{1-\tilde{c}_{ve}}{c_{ve}-\tilde{c}_{ve}}\right)\right) + CM_1 \text{ for } z \in$$
$$\partial \Omega \backslash D,$$

(ii) $|h_{2,err}(z)| \le 2\epsilon$ for $z \in D.$ $\quad$ EQUATION 32

On other hand, there exists a harmonic function $\omega(z)$ satisfying $$\omega(z) = \begin{cases} 0 & \text{for } z \in D \\ 1 & \text{for } z \in \partial \Omega D \end{cases},$$

and for $u \in (c_{ke}, \tilde{c}_{ve})$, $$\omega(u)\frac{4}{\pi}\arctan \sqrt{\frac{2(u-c_{ke})(\tilde{c}_{ve}-\tilde{c}_{vb})}{(\tilde{c}_{ve}-\tilde{c}_{vb})^2-(2c_{ke}-\tilde{c}_{ve}-\tilde{c}_{vb})(2u-\tilde{c}_{ve}-\tilde{c}_{vb})}}$$

EQUATION 33

Therefore, by Nevanlinna's principle, for $u \in (c_{ke}, \tilde{c}_{ve})$ $$|h_{2,err}(u)| \le \left\{M_2\left(\ln\left(\frac{\tilde{c}_{vb}+1}{\tilde{c}_{vb}-c_{vb}}\right)+\ln\left(\frac{1-\tilde{c}_{ve}}{c_{ve}-\tilde{c}_{ve}}\right)\right)+CM_1\right\}^{\omega(u)}(2\varepsilon)^{1-\omega(u)}$$

EQ. 34 and $$|h_{err}(u)| \le \varepsilon + \left\{M_2\left(\ln\left(\frac{\tilde{c}_{vb}+1}{\tilde{c}_{vb}-c_{vb}}\right)+\ln\left(\frac{1-\tilde{c}_{ve}}{c_{ve}-\tilde{c}_{ve}}\right)\right)+CM_1\right\}^{\omega(u)}(2\varepsilon)^{1-\omega(u)}$$

EQ. 35

In some embodiments, in order that for $u \in (c_{ke}, \tilde{c}_{ve})$ and $0 < \omega(u) < 1$, $\omega(u) \to 1$ as $u \to \tilde{c}_{ve}$. EQUATION 35 implies that the reconstruction of $f(u)$ for $u \in (c_{ke}, c_{ve})$ is stable near $c_{ke}$ and probably less stable near $c_{ve}$.

Singular Value Decomposition.

EQUATION 8 can be rewritten as $$g_w(u) = -\frac{g(u)}{2\pi} = PV \int_{c_{sb}}^{c_{se}} ch_{\mu 0}(u-\tilde{u})f(\tilde{u})d\tilde{u},\ u \in (c_{vb}, c_{ve})$$

EQ 36 and the u-axis can be discretized with a uniform sampling interval $\delta$ satisfying sampling theorem for both $f(u)$ and $g_w(u)$. Denote $f(u)$ at the discrete sampling points on the interval $(c_{sb}, c_{se})$ as $f_1, f_2, \ldots, f_n, \ldots, f_N$. Also, denote $g_w(u)$ at sampling points on the interval $(c_{vb}, c_{ve})$ as $g_1, g_2, \ldots g_m, \ldots g_M$.

Eq. (36) can be then discretized as $$G = AF$$

EQ 37 where $$F = [f_1 f_2 \ldots f_n \ldots f_n]^T$$

EQ 38

$$G = [g_1 g_2 \ldots g_m \ldots g_M]^T$$

EQ 39

$$A = \begin{bmatrix} A_{1,1} & \cdots & A_{1,n} & \cdots & A_{1,N} \\ \vdots & \ddots & \vdots & \ddots & \vdots \\ A_{m,1} & \cdots & A_{m,n} & \cdots & A_{m,N} \\ \vdots & \ddots & \vdots & \ddots & \vdots \\ A_{M,1} & \cdots & A_{M,n} & \cdots & A_{M,n} \end{bmatrix}$$

EQ 40

In EQUATIONS 38 and 39, "T" represents the transpose operator, and in EQUATION 40 $A_{m,n}$ represents the weighting coefficient of $f_n$. Let $u(f_n)$ and $u(g_m)$ be the coordinates on the u-axis for $f_n$ and $g_m$.

Based on the discrete Hilbert Kernel formulated, we can write $A_{m,n}$ as $$A_{m,n} = \begin{cases} \dfrac{e^{\mu_0 u_{m,n}^d}+e^{-\mu_0 u_{m,n}^d}}{\pi u_{m,n}^d/\delta} & u_{m,n}^d/\delta \text{ is odd} \\ 0 & \delta \text{ is even} \end{cases}$$

EQ 41 with $$u_{m,n}{}^d = u(g_m) - u(f_n)$$

EQ 42

With the sampling method of the present invention, $u_{m,n}{}^d/\delta$ always produces integers, and the case $u_{m,n}{}^d/\delta=0$ in EQUATION 42 exactly corresponds to the singular point in the Cauchy principal integral in EQUATION 36. Because $f(u)$ can be known on $(c_{vb}, c_{ke})$, F may be divided into two parts $$F = \begin{pmatrix} F^k \\ F_u \end{pmatrix}$$

EQ 43 where $F^k$ is the known part on the sampling points in $(c_{vb}, c_{ke})$, while $F^u$ is the unknown part on the sampling points in $(c_{sb}, c_{se})/(c_{vb}, c_{ke})$. Correspondingly, the matrix A can be divided into two parts $$A = (A^k A^u)$$

EQ 44

Then, one can immediately arrive at a linear equation system $$\overline{A}\overline{F} = \overline{G}$$

EQ 45 with $\overline{G} = G - A^k F^k$, $\overline{A} = A^u$ and $\overline{F} = F^u$.

Although EQUATION 45 is generally ill-posed, we can still stably reconstruct the part of $\overline{F}$ in the interval $(c_{ke}, c_{ve})$ using the singular value decomposition (SVD) method [19, 20]. Note that the dimension of $\overline{G}$ is $\overline{M} = M$. If the dimension of $\overline{F}$ is $\overline{N}$, the dimension of $\overline{A}$ will be $\overline{M} \times \overline{N}$. According to the SVD theory [19-21], the matrix $\overline{A}$ has a SVD decomposition in the following form $$\overline{A} = U\Lambda V^T$$

EQ 46 where U and V are orthogonal matrices of $\overline{M} \times \overline{M}$ and $\overline{N} \times \overline{N}$ respectively, and $\Lambda$ is an $\overline{M} \times \overline{N}$ diagonal matrix whose diagonal elements $\lambda_q$ satisfying $\lambda_1 \ge \ldots \ge \lambda_q \ge \ldots \ge \lambda_Q$, $Q = \min(\overline{M}, \overline{N})$. In this way, a stable numerical solution for $\overline{F}$ can be obtained, $$\overline{F} = \hat{F}^u = V\Lambda^{-1}U^T\overline{G}$$

EQ 47 where $\Lambda^{-1}$ is a diagonal matrix of $\overline{N} \times \overline{M}$ whose diagonal elements $\lambda_q^{-1}$ are defined as:

$$\lambda_q^{-1} = \begin{cases} 1/\lambda_q & \lambda_q > \varepsilon \\ 0 & \lambda_q \le \varepsilon \end{cases}$$

EQ 48 and $\varepsilon > 0$ is a free small constant parameter. The system defined by EQUATIONS 47 and 48 can be called a truncated SVD (TSVD), which is a special case of regularization.

Numerical Analysis.

The present invention numerically analyzes the stability of Theorem 1 from a signal processing viewpoint. In certain embodiments, the unknown $f(u)$ and known $g(u)$ are linked by EQUATION and $f(u)$ is assumed to be smooth. Based on the sampling theorem in the classical signal processing theory, $f(u)$ can be exactly recovered from its values at sampling points if (i) $f(u)$ can be band-limited and (ii) the sampling frequency may not be smaller than the Nyquist frequency. In addition to the smoothness of $f(u)$ the present invention can further assume that $f(u)$ may be essentially band-limited, which may be reasonable in most practical engineering applications. Hence, the present invention can stably reconstruct $f(u)$ at its finite sampling points on the interval $(c_{vb}, c_{ve})$ using the aforementioned SVD method.

When $\overline{G} = \overline{A}\overline{F} = A^u F^u$, it can be that $$\hat{F}^u - F^u = V\Lambda^{-1} U^T A^u F^u - F^u = (V\Lambda^{-1} U^T A^u - I^u) F^u \qquad \text{EQ 49}$$

where $I^u$ represents an $\overline{N} \times \overline{N}$ unit diagonal matrix. Let $E^u = \hat{F}^u - F^u$ as the error vector of $F^u$, and $S^u = V\Lambda^{-1} U^T A^u - I^u$ as an $\overline{N} \times \overline{N}$ matrix. Then, EQUATION 49 can be reduced as $$E^u = S^u F^u \qquad \text{EQ 50}$$

For any $1 \leq \overline{n} \leq \overline{N}$, the absolute reconstruction error can be expressed as $$|E_{\overline{n}}^u| = \left| \sum_{n'=1}^{N} S_{\overline{n},n'}^u F_{n'}^u \right| \leq \sum_{n'=1}^{N} |S_{\overline{n},n'}^u| \, |F_{n'}^u| \leq \left( \sum_{n'=1}^{N} |S_{\overline{n},n'}^u| \right) F_{max}^u = C_{\overline{n}}^{Eu} F_{max}^u \qquad \text{EQ 51}$$

where $F_{max}^u$ represents the maximum absolute value of the elements in $F^u$, and $$C_{\overline{n}}^{Eu} = \sum_{n'=1}^{N} |S_{\overline{n},n'}^u|.$$

Because $C_{\overline{n}}^{EU}$ reflects the accuracy of the reconstructed $\hat{F}^u$, we call it the precision measure in the present invention.

Next, considering the case of noisy data, and assuming that $$G^n = G + W^g, |W_m^g| < \epsilon, \qquad \text{EQ 52}$$

$$F^{nk} = F^k + W^{fk}, |W_n^{fk}| < \epsilon, \qquad \text{EQ 53}$$

where $\epsilon$ defines the maximum noise magnitude. Recall that $\overline{G} = G - A^k F^k$ and the noise expression of $\overline{G}$ can be written as $$\overline{G}^n = W^g - A^k W^{fk} \qquad \text{EQ 54}$$

Finally, based on EQUATION 47, the noise in the reconstructed image can be expressed as $$\hat{F}^{un} = V\Lambda^{-1} U^T (W^g - A^k W^{fk}) \qquad \text{EQ 55}$$

which can be further reduced as $$\hat{F}^{un} = P^{un} W^{un} \qquad \text{EQ 56}$$

with $P^{un} = (V\Lambda^{-1} U^T - V\Lambda^{-1} U^T A^k)$ and $$W^{un} = \begin{pmatrix} W^g \\ W^{fk} \end{pmatrix}.$$

Clearly, the dimension of $\hat{F}^{un}$ is $\overline{N} \times 1$. Assume that the dimension of $W^{un}$ is $\tilde{M} \times 1$ the dimension of $P^{un}$ must be $\overline{N} \times \tilde{M}$. For any $1 \leq \overline{n} < \overline{N}$, the absolute magnitude of noise in the image can be further expressed as:

$$|\hat{F}_{\overline{n}}^{un}| = \left| \sum_{\tilde{m}=1}^{\tilde{M}} P_{\overline{n},\tilde{m}}^{un} W_{\tilde{m}}^{un} \right| \leq \sum_{\tilde{m}=1}^{\tilde{M}} |P_{\overline{n},\tilde{m}}^{un}| |W_{\tilde{m}}^{un}| \leq \sum_{\tilde{m}=1}^{\tilde{M}} |P_{\overline{n},\tilde{m}}^{un}| \epsilon = C_{\overline{n}}^{Nu} \epsilon, \qquad \text{EQ 57}$$

where $$C_{\overline{n}}^{Nu} = \sum_{\tilde{m}=1}^{\tilde{M}} |P_{\overline{n},\tilde{m}}^{un}|$$

and $C_{\overline{n}}^{Nu}$ is called the stability measure in this disclosure. By evaluating the values of $C_{\overline{n}}^{Nu}$, we can directly reveal the stability of our algorithm for interior reconstruction of SPECT.

To demonstrate the exactness and stability of interior reconstruction of SPECT in the present invention, $c_{sb} = -1$, $c_{se} = 1$, $c_{vb} = -0.6$, $c_{ve} = 0.6$ and $c_{ke} = -0.2$ are set for numerical computation. Assume that the number of sampling points on $[-1,1]$ is N and the small constant in the TSVD method is $\epsilon$. For different combinations of N, $\epsilon$ and $\mu_0$, we computed the precision and stability measures $C_{\overline{n}}^{Eu}$ and $C_{\overline{n}}^{Nu}$ as shown in FIGS. 4 and 5, respectively. Because $f(u)$ was known on $(c_{vb}, c_{ke})$, the corresponding portions of $C_{\overline{n}}^{Eu}$ and $C_{\overline{n}}^{Nu}$ in the interval $(c_{vb}, c_{ke})$ were set to 0. From FIGS. 4 and 5, the following three comments can be made. First, there are little differences in terms of the precision and stability measures with respect to the number of sampling points on the whole support of $f(u)$. If the number N continuously increases, the sampling interval $\delta$ will become smaller and smaller. Eventually, the continuous case when N→∞ is reached. It is expected that there would still be little difference in terms of the precision and stability measures of N→∞ from what can be obtained (which is of course a numerical observation lack of mathematical rigor). Second, the precision measure $C_{\overline{n}}^{Eu}$ in FIG. 4 is very close to zero in the interval $[c_{ke}, c_{ve})$, especially the portions near $c_{ke}$. When the constant $\epsilon$ is reduced in the TSVD method, the precision measure $C_{\overline{n}}^{Eu}$ would decrease in the interval $[c_{ke}, c_{ve})$, which means a higher accuracy. Undoubtedly, $C_{\overline{n}}^{Eu}$ should ideally approach zero on the interval $[c_{ke}, c_{ve})$ when $\epsilon \to 0$. Meanwhile, a small constant attenuation parameter $\mu_0$ yields a better precision. Third, the stability measure in FIG. 5 was smaller on the interval $[c_{ke}, c_{ve})$ than elsewhere (especially the portion near $c_{ke}$), which means a better stability. If the constant $\epsilon$ is continuously decreased in the TSVD method, the stability measure would correspondingly increase in an order of $1/\epsilon$, which means the stability would become worse and worse.

In this present invention, an interior reconstruction technique for SPECT in a parallel-beam geometry is provided. Using a rebinning scheme, EQUATION 5 can be extended into a fan-beam geometry and other variants, such as the varying focal-length fan-beam geometry. A major difference lies in the involved Jacobian factor of EQUATION 5 in the backprojection step, while the generalized Hilbert transform based reconstruction method may remain the same as that for parallel-beam imaging. Using analytic techniques similar to our generalized backprojection filtration method, our interior SPECT methodology can be further extended to more complex cone-beam configurations and more general focal spot trajectories.

When the reconstruction formula was derived and the exactness and stability analyzed, in some embodiments, it is possible to assume a uniform attenuation map. Without giving a detailed proof and analysis, it should be pointed out that in other embodiments, similar results can be obtained for a nonuniformly attenuated background. In that case, both analytic continuation and SVD techniques remain important tools to analyze the uniqueness, exactness and stability, as well as to reconstruct a distribution of radioactive sources. In addition to the SVD method disclosed in this application, other reconstruction methods, such as POCS, can be also developed for reconstruction from generalized attenuated Hilbert transform data.

As another important nuclear medicine imaging modality, positron emission tomography (PET) produces 3D images of functional and cellular features in the body. Different from SPECT, a radio-active source emits pairs of particles in opposite directions, and they are detected in the coincidence mode, i.e., only events with two particles arriving at opposite detectors within a narrow time window are counted. Thus, the projection model of PET can be written as $$P_o(\theta, s) = e^{\int_{-\infty}^{+\infty} \mu(s\theta + \bar{t}\theta^\perp)d\bar{t}} \int_{-\infty}^{\infty} f(s\theta + t\theta^\perp)dt. \quad \text{EQ 58}$$

After an attenuation correction, the both uniform and nonuniform PET reconstruction can be done as from CT projection data.

HOT SPECT.

In the embodiments discussed above, the limitation of knowing and clearly defining the object boundaries exist. Although the CT numbers of certain sub-regions such as air in a trachea and blood in an aorta can be indeed assumed, how to obtain precise knowledge of a sub-region can be difficult in important cases such as in contrast-enhanced/functional studies. Therefore, it would be very valuable to develop more powerful interior tomography techniques. Fortunately, the compressive sampling (CS) theory has recently emerged which shows that high-quality signals and images can be reconstructed from far fewer data than what is usually considered necessary according to the Nyquist sampling theory. The main idea of CS is that most signals are sparse in an appropriate system, that is, a majority of their coefficients are close or equal to zero, when represented in an appropriate domain. In light of the CS theory and using the specific gradient transform, we proved that it is possible to accurately reconstruct an ROI only from truncated projections by minimizing the total variation (TV) if the ROI is piecewise constant, without knowledge of any known sub-region in the ROI which. Very recently we extended this piece-wise constant result to allow a piecewise polynomial model and the inventive interior tomography systems and methods by the high order TV (HOT) minimization. See, e.g., "High Order Total Variation Minimization for Interior SPECT," Yang Jiansheng et al. 2010, which is incorporated herein by reference in its entirety.

Figure 8:
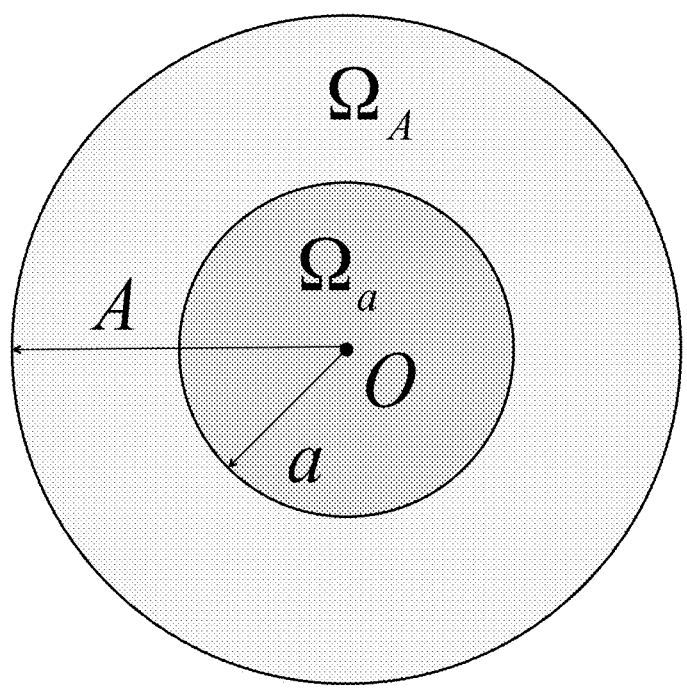
FIG. 8 is a schematic representation of the configuration of a compact support and a ROI for interior SPECT tomography.

HOT-minimization-based interior tomography can be generalized for interior SPECT. The present invention seeks to accurately reconstruct an ROI only from the uniformly attenuated local SPECT projections through the HOT minimization under the assumption that the underlying distribution function is piecewise polynomial. Without loss of generality, in certain embodiments, the following conditions are assumed:

Condition (1):

An object image $f_0(x)$ is compactly supported on a disc $\Omega_A = \{x=(x_1,x_2) \in \mathbb{R}^2 : |x| < A\}$, where A is a positive constant. Furthermore, $f_0(x)$ is a piecewise smooth function; that is, $\Omega_A$ can be partitioned into finitely many sub-domains $\{D_j\}_{j=1}^{N_0}$, such that $f_0(x)$ is smooth with bounded derivatives in each $D_j$;

Condition (2):

An internal ROI is a smaller disc, $\Omega_a = \{x=(x_1,x_2) \in \mathbb{R}^2 : |x| < a\}$ as shown in FIG. 8, where a is a positive constant and a<A;

Condition (3):

Attenuated projections through the ROI $$R_\mu f_0(s, \theta) = \int_{-\infty}^{\infty} f_0(s\theta + t\theta^\perp)e^{-\mu t} dt, -a < s < a, \theta \in S^1, \quad \text{EQUATION 59}$$

are available, where μ is a constant attenuation coefficient, and $$\theta = (\cos\varphi, \sin\varphi), \theta^\perp = (-\sin\varphi, \cos\varphi), 0 \le \varphi < 2\pi.$$

The interior SPECT with uniformly attenuated local projection data is to find an image $f(x)$ such that Condition (4):

$f(x)$ is a piecewise smooth function and compactly supported on the disc $\Omega_A$;

Condition (5):

$$R_\mu f(s,\theta) = R_\mu f_0(s,\theta), -a<s<a, \theta \in S^1.$$

It is well known that under Conditions (4) and (5) the interior problem does not have a unique solution. The following theorem characterizes the structure of solutions to the interior SPECT problem.

Theorem 2.

Any image $f(x)$ satisfying Conditions (4) and (5) can be written as $f(x)=f_0(x)+u(x)$ for $x \in \mathbb{R}^2$, where $u(x)$ is an analytic function in the disc $\Omega_a$, and $R_\mu u(s,\theta)=0, -a<s<a, \theta \in S^1$. Such an image $f(x)$ is named a candidate image, and correspondingly $u(x)$ an ambiguity image.

Proof for Theorem 2.

Let $u(x)=f(x)-f_0(x)$. Clearly, $u(x)$ is a piecewise smooth function and compactly supported on the disc $\Omega_A$ by Condition (1) and (4), and $$R_\mu u(s,\theta)=0, -a<s<a, \theta \in S^1 \quad \text{EQUATION 60}$$

By Tretiak and Metz's Inversion formula, which was derived from the shift property (5) and Corollary 2, we have $$u(x) = \frac{1}{4\pi^2} \int_0^{2\pi} e^{-\mu x \cdot \theta^\perp} \int_{a<|s|\le A} \frac{\cos(\mu(s-x\cdot\theta))}{s-x\cdot\theta} \frac{\partial R_\mu u(s, \theta)}{\partial s} ds\, d\varphi. \quad \text{EQUATION 61}$$

the term $$\frac{\cos(\mu_0(s-x\cdot\theta))}{s-x\cdot\theta} e^{-\mu_0 x \cdot \theta^\perp}$$

in the integral is analytic, which can be expressed in a power series. Therefore, u(x) can also be expressed in a power series, that is, $$u(x) = \sum_{k=0}^{\infty} \sum_{k_1+k_2=k} c_{k_1,k_2} x_1^{k_1} x_2^{k_2}. \qquad \text{EQUATION 62}$$

Hence, the function u(x) is an analytic function in $\Omega_a$. From now on, let u(x) always represent an ambiguity image unless otherwise stated. We will rely on the HOT minimization to solve the interior SPECT problem with uniformly attenuated local projection data under the assumption that $f_0(x)$ is piecewise polynomial in a ROI $\Omega_a$.

If an object image $f_0(x)$ is piecewise polynomial in ROI $\Omega_a$, we can prove that $f_0(x)$ is the only candidate image that minimizes the HOT. First, let us prove that if an ambiguity image is polynomial in $\Omega_a$, then it must be zero. This result will be formally stated as Theorem 3. In order to prove Theorem 3, we will need Lemmas 1, 2 and 3.

Lemma 1.

Suppose that a is a positive constant. If (a) g(z) is an analytic function in $\mathbb{C}\setminus(-\infty,-a]\cup[a,+\infty)$; (b) p(x) is a polynomial function; (c)

$$g(x) = \frac{1}{\pi} PV \int_{|t|<a} \frac{p(t)}{x-t} dt,$$

for x∈(-a,a), then $$\lim_{y\to 0+} \text{Im}(g(x+iy)) = p(x),$$

for x∈(-∞,-a)∪(a,+∞).

Lemma 2.

Assume that a is a positive constant. If (a) g(z) is an analytic function in $\mathbb{C}\setminus(-\infty,-a]\cup[a,+\infty)$; (b) p(x) is a polynomial function; (d)

$$g(x) = \frac{1}{\pi} PV \int_{|t|<a} \frac{\cosh(\mu(x-t))p(t)}{x-t} dt,$$

for x∈(-a,a), then we have $$\lim_{y\to 0+} \text{Im}(g(x+iy)) = p(x),$$

for x∈(-∞,-a)∪(a,+∞).

Proof of Lemma 2:

g(z) can be rewritten as g(z)=g_1(z)+g_2(z), for $$z\in \mathbb{C}\setminus(-\infty,-a]\cup[a,+\infty), \qquad \text{EQUATION 63}$$

where (i) $g_1(z)$ is an analytic function in $$\mathbb{C}\setminus(-\infty,-a]\cup[a,+\infty), \text{and}$$

$$g_1(x) = \frac{1}{\pi} PV \int_{|t|<a} \frac{p(t)}{x-t} dt, \text{ for } x\in(-a,a); \qquad \text{EQUATION 64}$$

(ii) $g_2(z)$ is an analytic function in $\mathbb{C}$, and $$g_2(z) = \frac{1}{\pi} \int_{|t|<a} \frac{[\cosh(\mu(z-t))-1]p(t)}{z-t} dt, \text{ for } z\in\mathbb{C}.$$

Using Lemma 1, we obtain $$\lim_{y\to 0+} \text{Im}(g_1(x+iy)) = p(x), \qquad \text{EQUATION 66}$$

for x∈(-∞,-a)∪(a,+∞).

Because of the continuity of $g_2(z)$ in $\mathbb{C}$, it is clear that $$\lim_{y\to 0+} \text{Im}(g_2(x+iy)) = \text{Im}(g_2(x)) = 0, \text{ for } x\in(-\infty,+\infty). \qquad \text{EQUATION 67}$$

Therefore, we have $$\lim_{y\to 0+} \text{Im}(g(x+iy)) = \lim_{y\to 0+} \text{Im}(g_1(x+iy)) + \lim_{y\to 0+} \text{Im}(g_2(x+iy)) = p(x),$$

for x∈(-∞,-a)∪(a,+∞), $\qquad$ EQUATION 68 which completes the proof.

Lemma 3

Assume that a and A are positive constants with a<A. If a single variable function $v(x)\in L^\infty(\mathbb{R})$ satisfies (e) v(x) is compactly supported in [-A,A]; (f) v(x)=p(x) for x∈(-a,a), where p(x) is a polynomial function; (g) $H_\mu v(x)=0$ for x∈(-a,a), where $H_\mu v(x)$ is the generalized Hilbert transform of v(x), that is $$H_\mu v(x) = \frac{1}{\pi} PV \int_{\mathbb{R}} \frac{\cosh(\mu(x-s))v(s)}{x-s} ds; \text{ Then } v(x) = 0.$$

Proof of Lemma 3:

The function $$g(z) = \frac{1}{\pi} \int_{|t|\geq a} \frac{\cosh(\mu(t-z))v(t)}{t-z} dt, \qquad \text{EQUATION 69}$$

is analytic on $\mathbb{C}\setminus(-\infty,-a]\cup[a,+\infty)$. Then, g(z) can be rewritten as $g(z)=g_1(z)+g_2(z)$, for $z\in\mathbb{C}\setminus(-\infty,-a]\cup[a,+\infty)$ $\qquad$ EQUATION 70

Where:

(i) $g_1(z)$ is an analytic function in $\mathbb{C} \setminus (-\infty,-a] \cup [a,+\infty)$, and $$g_1(z) = \frac{1}{\pi} \int_{|t| \geq a} \frac{v(t)}{t-z} dt,$$

for $z \in \mathbb{C} \setminus (-\infty,-a] \cup [a,+\infty)$; EQUATION 71

(ii) $g_2(z)$ is an analytical function in $\mathbb{C}$, and $$g_2(z) = \frac{1}{\pi} \int_{|t| \geq a} \frac{[\cosh(\mu(t-z))-1]v(t)}{t-z} dt, \text{ for } z \in \mathbb{C}.$$ EQUATION 72 with $g_1(z)$, we have for $y>0$, $$Im(g_1(x+iy)) =$$ EQUATION 73
$$\frac{1}{\pi} \int_{|t| \geq a} \frac{y}{(t-x)^2+y^2} v(t) dt = \frac{1}{\pi} \int_{\mathbb{R}} \frac{y}{(t-x)^2+y^2} \tilde{v}(t) dt,$$

where $$\tilde{v}(x) = \begin{cases} v(x), & x \in (-\infty,-a) \cup (a,\infty) \\ 0, & x \in [-a,a] \end{cases}.$$ EQUATION 74

Applying Theorem 1, we obtain $$\lim_{y \to 0^+} Im(g_1(x+iy)) = \tilde{v}(x) = v(x),$$

for a.e. $x \in (-\infty,-a) \cup (a,\infty)$. EQUATION 75

Using EQUATION 67, we have $$\lim_{y \to 0^+} Im(g(x+iy)) = \lim_{y \to 0^+} Im(g_1(x+iy)) = v(x),$$ EQ. 76 for a.e. $x \in (-\infty,-a) \cup (a,\infty)$.

On the other hand, for $x \in (-a,a)$, $$g(x) = \frac{1}{\pi} PV \int \frac{\cosh(\mu(t-x))v(t)}{t-x} dt - \frac{1}{\pi} PV \int_{|t|<a} \frac{\cosh(\mu(t-x))v(t)}{t-x} dt =$$
$$-H_\mu v(x) + \frac{1}{\pi} PV \int_{|t|<a} \frac{\cosh(\mu(t-x))p(t)}{x-t} dt =$$
$$\frac{1}{\pi} PV \int_{|t|<a} \frac{\cosh(\mu(t-x))p(t)}{x-t} dt.$$

Using Lemma 3, we obtain $$\lim_{y \to 0^+} Im(g_1(x+iy)) = p(x), \ x \in (-\infty,-a) \cup (a,+\infty).$$ EQUATION 78

Combining the above equations, we have $$v(x) = p(x), \text{ for a.e. } x \in (-\infty,\infty).$$ EQUATION 79

Condition (e) and EQUATION 79 imply $$p(x)=0, x \in (-\infty,-A) \cup (A,\infty).$$ EQUATION 80

Because p(x) is polynomial, it follows that p(x)=0. Therefore, $$v(x)=0, \text{ for a.e } x \in (-\infty,\infty).$$ EQUATION 81

Theorem 3

If an artifact image u(x) satisfies (a) with $x \in \Omega_a$, where p(x) is a 2-D polynomial function; (b) $R_\mu u(s,\theta)=0$ with $s \in (-a,a)$, then u(x)=0.

Proof of Theorem 3.

Figure 9:
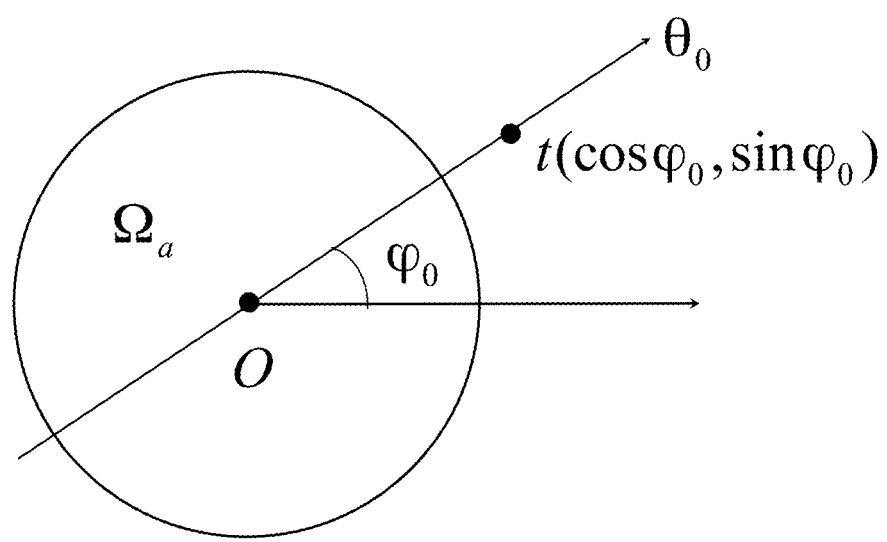
FIG. 9 is a schematic representation of a radial line through the origin.

As illustrated in FIG. 9, for an arbitrary $\phi_0 \in [0,\pi)$, let $L_{\theta_0}$ denote the line through the origin and tilted at $\theta_0 = (\cos \phi_0, \sin \phi_0)$. When u(x) is restricted to the line $L_{\theta_0}$, it can be expressed as $$u_{\theta_0}(t) = u(t(\cos \phi_0, \sin \phi_0)), t \in (-\infty,\infty).$$ EQUATION 82

By the relationship between the differentiated backprojection of the attenuated projection data and the generalized Hilbert transform of the image [5], we have $$H_\mu u_{\theta_0}(t) = -\frac{1}{2\pi} \int_{\varphi_0 - \frac{\pi}{2}}^{\varphi_0 + \frac{\pi}{2}} \frac{\partial R_\mu u(s,\theta)}{\partial s} \bigg|_{s=x^t_{\theta_0} \cdot \theta} e^{-x^t_{\theta_0} \cdot \theta^\perp} d\varphi,$$ EQUATION 83

Where $x^t_{\theta_0} = t(\cos \phi_0, \sin \phi_0), \theta = (\cos \phi, \sin \phi), \theta^\perp = (-\sin \phi, \cos \phi)$, EQUATION 84

$$H_\mu u_{\theta_0}(t) = \frac{1}{\pi} PV \int \frac{\cosh(\mu(t-s))u_{\theta_0}(s)}{t-s} ds.$$ EQUATION 85

By (a) and EQUATION 82, we have $$u_{\theta_0}(t) = p(t(\cos \phi_0, \sin \phi_0)), \text{ for } t \in (-a,a),$$ EQUATION 86 where $p(t(\cos \phi_0, \sin \phi_0))$ is a polynomial function with respect to t. By (b) and EQUATION 83, we have $$H_\mu u_{\mu_0}(t)=0, \text{ for } t \in (-a,a).$$ EQUATION 87

Using Lemma 3, we obtain $$u_{\theta_0}(t)=0.$$ EQUATION 88

Therefore, $$u(x)=0,$$ EQUATION 89 which completes the proof.

Lemma 4

Figure 10:
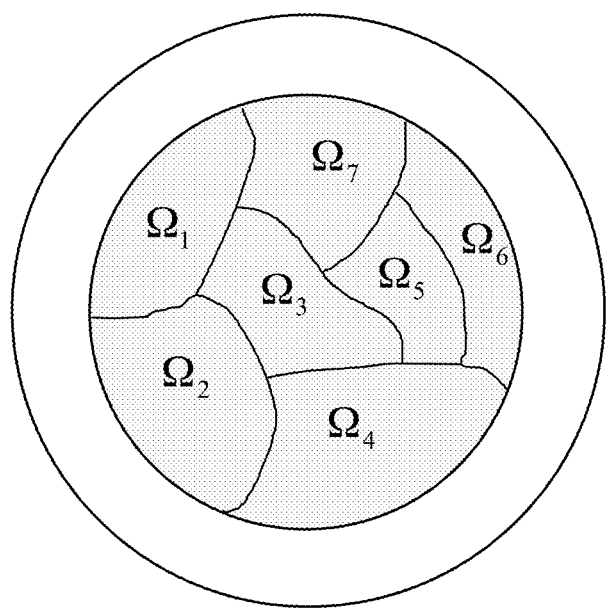
FIG. 10 is a schematic diagram of ROI consisting of 7 sub-domains.

Suppose that $f_0(x)$ is piecewise constant in ROI $\Omega_a$; that is, $\Omega_a$ can be decomposed into finitely many sub-domains $\{\Omega_i\}_{i=1}^m$ (FIG. 10) such that $$f_0(x) = f_i(x) = c_i, \text{ for } x \in \Omega_i, 1 \leq i \leq m,$$ EQUATION 90 and each sub-domain $\Omega_i$ is adjacent to its neighboring sub-domains $\Omega_j$, with piecewise smooth boundaries $\Gamma_{i,j}$, $j \in N_i$. For any candidate image $f(x) = f_0(x) + u(x)$, where u(x) is an arbitrary ambiguity image, let $$TV(f) = \sup\{\int_{\Omega_a} f \text{ div } \phi dx : \phi \in C_0^1(\Omega_a)^2, |\phi| \leq 1 \text{ in } \Omega_a\},$$ EQUATION 91 where $C_0^1(\Omega_a)^2 = C_0^1(\Omega_a) \times C_0^1(\Omega_a)$, then $$TV(f) = \sum_{i=1}^{m} \sum_{j>i, j \in N_i} |c_i - c_j||\Gamma_{i,j}| + \int_{\Omega_a} \sqrt{\left(\frac{\partial u}{\partial x_1}\right)^2 + \left(\frac{\partial u}{\partial x_2}\right)^2} dx_1 dx_2. \qquad \text{EQUATION 92}$$

Under the assumption that $f_0(x)$ is piecewise constant in ROI $\Omega_a$, through the TV minimization we can establish the uniqueness of interior SPECT as follows.

Theorem 4

Suppose that $f_0(x)$ is piecewise constant in a ROI $\Omega_a$, as defined by Eq. (3.28). If h(x) is a candidate image and $$TV(h) = \min_{f=f_0+u} TV(f),$$

then $h(x)=f_0(x)$ for $x \in \Omega_a$

Proof of Theorem 4:

Let $$h(x)=f_0(x)+u_1(x). \qquad \text{EQUATION 93}$$

where $u_1(x)$ is an ambiguity image. By Lemma 4, we have $$TV(h) = \sum_{i=1}^{m} \sum_{j>i, j \in N_i} |c_i - c_j||\Gamma_{i,j}| + \int_{\Omega_a} \sqrt{\left(\frac{\partial u_1}{\partial x_1}\right)^2 + \left(\frac{\partial u_1}{\partial x_2}\right)^2} dx_1 dx_2. \qquad \text{EQUATION 94}$$

Since $$TV(h) = \min_{f=f_0+u} TV(f), \qquad \text{EQUATION 95}$$

and $$\min_{f=f_0+u} TV(f) = TV(f_o) = \sum_{i=1}^{m} \sum_{j>i, j \in N_i} |c_i - c_j||\Gamma_{i,j}|. \qquad \text{EQUATION 96}$$

we have $$\int_{\Omega_2} \sqrt{\left(\frac{\partial u_1}{\partial x_1}\right)^2 + \left(\frac{\partial u_1}{\partial x_2}\right)^2} dx_1 dx_2 = 0; \qquad \text{EQUATION 97}$$

that is $$\frac{\partial u_1}{\partial x_1} = \frac{\partial u_1}{\partial x_2} = 0, \text{ in } \Omega_a. \qquad \text{EQUATION 98}$$

Therefore, there exists a constant c such that $$u_1(x)=c, \text{ in } \Omega_a. \qquad \text{EQUATION 99}$$

that is, $u_1(x)$ is a 0-th order polynomial in $\Omega_a$. By Theorem 2, we have $$u_1(x)=0. \text{ in } \Omega_a. \qquad \text{EQUATION 100}$$

Thus, we have $$h(x)=f_0(x) \text{ for } x \in \Omega_a. \qquad \text{EQUATION 101}$$

An expression for high order TV (HOT) was previously introduced. In certain embodiments, the present invention provides an alternative expression. We define the n+1-th ($n \geq 1$) order TV as the limit of the following sum:

$$HOT_{N+1}(f) = \underset{(\max_{1 \leq k \leq M} diam(Q_k) \downarrow)}{\lim sup} \sum_{k=1}^{M} I_k^{n+1}(f), \qquad \text{EQUATION 102}$$

where $\{Q_k\}_{k=1}^{M}$ is an arbitrary partition of $\Omega_a$, diam($Q_k$) the diameter of $Q_k$, and $$I_k^{n+1}(f) = \min\{I_{k,1}(f), I_{k,2}^{n+1}(f)\}, \qquad \text{EQUATION 103}$$

$$I_{k,1}(f) = \sup\left\{\int_{Q_k} f \, div g \, dx : g = (g_l)_{l=1}^{2} \in C_0^{\infty}(Q_k)^2, \right. \qquad \text{EQUATION 104}$$

$$\left. |g| \leq 1 \text{ in } Q_k\right\},$$

$$div g = \sum_{l=1}^{2} \frac{\partial g_l}{\partial x_l}, |g| = \sqrt{\sum_{l=1}^{2} |g_l|^2}; \qquad \text{EQUATION 105}$$

$$I_{k,2}^{n+1}(f) = \qquad \text{EQUATION 106}$$

$$sup\left\{\int_{Q_k} f \, div_{n+1} \overline{g} \, dx : \overline{g} = (\overline{g}_r)_{r=0}^{n+1} \in C_0^{\infty}(Q_k)^{n+2},\right.$$

$$\left. |\overline{g}| \leq 1 \text{ in } Q_k\right\},$$

$$div_{n+1} \overline{g} = \sum_{r=0}^{n+1} \frac{\partial^{n+1} \overline{g}_r}{\partial x_1^r \partial x_2^{n+1-r}}, |\overline{g}| = \sqrt{\sum_{r=0}^{n+1} |\overline{g}_r|^2}. \qquad \text{EQUATION 107}$$

Under the assumption that $f_0(x)$ is a piecewise n-th ($n \geq 1$) order polynomial function in an ROI $\Omega_a$, through the HOT minimization we can establish the uniqueness of interior SPECT, just as what we have done for interior CT. First, we will derive an explicit formula of $HOT_{n+1}(f)$ for any candidate image $f$ under the assumption that $f_0(x)$ is a piecewise n-th ($n \geq 1$) order polynomial function in $\Omega_a$.

Lemma 5.

Suppose that $f_0(x)$ is a piecewise n-th ($n \geq 1$) order polynomial function in $\Omega_a$; that is, $\Omega_a$ can be decomposed into finitely many sub-domains $\{\Omega_i\}_{i=1}^{m}$ (FIG. 10) such that $$f_0(x)=f_i(x), \text{ for } x \in \Omega_i, 1 \leq i \leq m, \qquad \text{EQUATION 108}$$

where $f_i(x)$ is a n-th order polynomial function, and each sub-domain $\Omega_i$ is adjacent to its neighboring sub-domains $\Omega_j$ with piecewise smooth boundaries $\Gamma_{i,j}$, $j \in N_i$. Then, for any candidate image $f(x)=f_0(x)+u(x)$, we have $$HOT_{n+1}(f) = \sum_{i=1}^{m} \sum_{j>i, j \in N_i} \int_{\Gamma_{i,l}} |f_i - f_j| ds +$$

$$\int_{\Omega_2} \min\left\{\sqrt{\sum_{r=0}^{n+1} \left(\frac{\partial^{n+1} f}{\partial x_1^r \partial x_2^{n+1-r}}\right)^2},\right.$$

$$\left.\sqrt{\left(\frac{\partial f}{\partial x_1}\right)^2 + \left(\frac{\partial f}{\partial x_2}\right)^2}\right\} dx,$$

EQUATION 109 where the second term is a Lebesgue integral.

Proof:

Note that $f(x)=f_0(x)+u(x)$, where $u(x)$ is an analytic function. Let $\{Q_k\}_{k=1}^M$ be an arbitrary partition of $\Omega_a$. First, let us consider $Q_k$ that covers a common boundary $\Gamma_{i,j}$ of a pair of neighboring sub-domains $\Omega_i$ and $\Omega_j$, and is contained in $\Omega_i \cup \Omega_j$ (FIG. 11A). The normal vector of the curve $\Gamma_{i,j}$ pointing from $\Omega_j$ towards $\Omega_i$ is denoted by $\theta^{i,j}=(\theta_1^{i,j}, \theta_2^{i,j})$. For $g=(g_l)_{l=1}^2 \in C_0^\infty(Q_k)^2$ we have $$\int_{Q_k} f \operatorname{div} g\, dx = \int_{Q_k \cap \Omega_i} f \operatorname{div} g\, dx + \int_{Q_k \cap \Omega_j} f \operatorname{div} g\, dx.$$

EQUATION 110

Performing integration by parts for the two terms on the right-hand side of Eq. (3.48) respectively and utilizing the fact that $g(x)=(0,0)$ near the boundary of $Q_k$, we have $$\int_{Q_k \cap \Omega_i} f \operatorname{div} g\, dx = -\int_{\Gamma_{i,j} \cap Q_k} (f_i)(x) + u(x))(g_1 \theta_1^{i,j} + g_2 \theta_2^{i,j}) ds -$$

$$\int_{Q_k \cap \Omega_i} \sum_{l=1}^{2} \frac{\partial f}{\partial x_l} g_l dx,$$

EQ. 111

$$\int_{Q_k \cap \Omega_j} f \operatorname{div} g\, dx = \int_{\Gamma_{i,j} \cap Q_k} (f_j(x) + u(x))(g_1 \theta_1^{i,j} + g_2 \theta_2^{i,j}) ds -$$

$$\int_{Q_k \cap \Omega_j} \sum_{l=1}^{2} \frac{\partial f}{\partial x_l} g_l dx.$$

EQ. 112

Inserting the three proceeding EQUATIONS, we obtain $$\int_{Q_k} f \operatorname{div} dx = \int_{\Gamma_{i,j} \cap Q_k} (f_j - f_i)(g_1 \theta_1^{i,j} + g_2 \theta_1^{i,j}) ds -$$

$$\int_{Q_k \cap \Omega_i} \sum_{l=1}^{2} \frac{\partial f}{\partial x_l} g_l dx - \int_{Q_k \cap \Omega_j} \sum_{l=1}^{2} \frac{\partial f}{\partial x_l} g_l dx.$$

EQ. 113

Furthermore, we have $$\sup_{g=(g_l)_{l=1}^2 \in C_0^\infty(Q_k)^2, |g| \leq 1 \text{ in } Q_k} \int_{\Gamma_{i,j} \cap Q_k} (f_j - f_i)(g_1 \theta_1^{i,j} + g_2 \theta_2^{i,j}) ds =$$

EQ. 114

$$\int_{\Gamma_{i,j} \cap Q_k} |f_j - f_i| ds,$$

$$\int_{Q_k \cap \Omega_i} \sum_{l=1}^{2} \frac{\partial f}{\partial x_l} g_l dx + \int_{Q_k \cap \Omega_j} \sum_{l=1}^{2} \frac{\partial f}{\partial x_l} g_l dx =$$

$$O(1)|Q_k \cap \Omega_i| + O(1)|Q_k \cap \Omega_j| = O(1)|Q_k|,$$

for $g=(g_l)_{l=1}^2 \in C_0^\infty(Q_k)^2, |g| \leq 1$ in $Q_k$

EQUATION 115 where $O(1)$ is a quantity bounded by a constant which depends only on $f(x)$.

Combining the above equations, we obtain $$I_{k,l}(f) = \int_{\Gamma_{i,j} \cap Q_k} |f_j - f_i| ds + O(1)|Q_k|.$$

EQUATION 116

On the other hand, for $\bar{g}=(\bar{g}_r)_{r=0}^{n+1} \in C_0^\infty(Q_k)^{n+2}$, repeatedly performing the 2-D integration by parts and utilizing the fact that $\bar{g}(x)=(0,\ldots,0)$ near the boundary of $Q_k$, we have $$\int_{Q_k} f \operatorname{div}_{n+1} \bar{g}\, dx =$$

EQUATION 117

$$\int_{Q_k \cap \Omega_i} f \operatorname{div}_{n+1} \bar{g}\, dx + \int_{Q_k \cap \Omega_j} f \operatorname{div}_{n+1} \bar{g}\, dx =$$

$$\sum_{l=1}^{n-1} (-1)^{l-1} \int_{\Gamma_{i,j} \cap Q_k} \left[ \sum_{r=0}^{l-1} \frac{\partial^{l-1}(f_j - f_i)}{\partial x_1^r \partial x_2^{l-1-r}} \right.$$

$$\frac{\partial^{n+1-l} \bar{g}_r}{\partial x_2^{n+1-l}} \theta_2^{i,j} + \frac{\partial^{l-1}(f_j - f_i)}{\partial x_1^{l-1}}$$

$$\left. \sum_{r=l}^{n+1} \frac{\partial^{n+1-l} \bar{g}_r}{\partial x_1^{r-l} \partial x_2^{n+1-r}} \theta_1^{i,j} \right] ds +$$

$$(-1)^{n+1} \int_{Q_k \cap \Omega_i} \sum_{r=0}^{n+1} \frac{\partial^{n+1} f}{\partial x_1^r \partial x_2^{n+1-r}} \bar{g}_r dx +$$

$$(-1)^{n+1} \int_{Q_k \cap \Omega_j} \sum_{r=0}^{n+1} \frac{\partial^{n+1} f}{\partial x_1^r \partial x_2^{n+1-r}} \bar{g}_r dx =$$

$$\sum_{l=1}^{n} (-1)^{l-1} \int_{\Gamma_{i,j} \cap Q_k} \left[ \sum_{r=0}^{l-1} \frac{\partial^{l-1}(f_j - f_i)}{\partial x_1^r \partial x_2^{l-1-r}} \right.$$

$$\frac{\partial^{n+1-l} \bar{g}_r}{\partial x_2^{n+1-l}} \theta_2^{i,j} + \frac{\partial^{l-1}(f_j - f_i)}{\partial x_1^{l-1}}$$

$$\left. \sum_{r=l}^{n+1} \frac{\partial^{n+1-l} \bar{g}_r}{\partial x_1^{r-l} \partial x_2^{n+1-r}} \theta_1^{i,j} \right] ds +$$

$$(-1)^n \int_{\Gamma_{i,j} \cap Q_k} \left[ \sum_{r=0}^{n} \frac{\partial^n (f_j - f_i)}{\partial x_1^r \partial x_2^{n-r}} \bar{g}_r \theta_2^{i,j} + \right.$$

$$\left. \frac{\partial^n (f_j - f_i)}{\partial x_1^n} \bar{g}_{n+1} \theta_1^{i,j} \right] ds +$$

$$(-1)^{n+1} \int_{Q_k \cap \Omega_i} \sum_{r=0}^{n+1} \frac{\partial^{n+1}}{\partial x_1^r \partial x_2^{n+1-r}} \bar{g}_r dx +$$

-continued $$(-1)^{n+1} \int_{Q_k \cap \Omega_j} \sum_{r=0}^{n+1} \frac{\partial^{n+1} f}{\partial x_1^r \partial x_2^{n+1-r}} \overline{g}_r dx.$$

Furthermore, we have $$(-1)^n \quad \text{EQUATION 118}$$

$$\int_{\Gamma_{i,j} \cap Q_k} \left[ \sum_{r=0}^{n} \frac{\partial^n (f_j - f_i)}{\partial x_1^r \partial x_2^{n-r}} \overline{g}_r \theta_2^{i,j} + \frac{\partial^n (f_j - f_i)}{\partial x_1^n} \overline{g}_{n+1} \theta_1^{i,j} \right]$$

$$ds = O(1) |\Gamma_{i,j} \cap Q_k|,$$

for $\overline{g} = (\overline{g}_r)_{r=0}^{n+1} \in C_0^\infty(Q_k)^{n+2}, |\overline{g}| \le 1$ in $Q_k$, $$(-1)^{n+1} \int_{Q_k \cap \Omega_j} \sum_{r=0}^{n-1} \frac{\partial^{n+1} f}{\partial x_1^r \partial x_2^{n+1-r}} \overline{g}_r dx +$$

$$(-1)^{n+1} \int_{Q_k \cap \Omega_j} \sum_{r=0}^{n+1} \frac{\partial^{n+1} f}{\partial x_1^r \partial x_2^{n+1-r}} \overline{g}_r dx =$$

$$O(1)|Q_k \cap \Omega_i| + O(1)|Q_k \cap \Omega_j| = O(1)|Q_k|,$$

for $\overline{g} = (\overline{g}_r)_{r=0}^{n+1} \in C_0^\infty(Q_k)^{n+2}, |\overline{g}| \le 1$ in $Q_k$, $I_{k,2}^{n+1}(f)$ was evaluated in several cases and lemma 5 was proven. Finally, we have the following Theorem 5 on the uniqueness of interior SPECT.

Theorem 5.

Suppose that $f_0(x)$ is a piecewise n-th (n≥1) order polynomial function in $\Omega_a$, as defined in Lemma 5. If h(x) is a candidate image and $$HOT_{n+1}(h) = \min_{f = f_0 + u_1} HOT_{n+1}(f)$$

which $u_1(x)$ is an arbitrary ambiguity image, then $h(x) = f_0(x)$ for $x \in \Omega_a$.

Proof of Theorem 5:

Let $h(x) = f_0(x) + u(x)$ for some ambiguity image u(x). By Lemma 5, we have $$HOT_{n+1}(f) \ge \sum_{i=1}^{m} \sum_{j>i, j \in N_i} \int_{\Gamma_{i,j}} |f_i - f_j| ds, \quad \text{EQUATION 119}$$

for $f = f_0(x) + u_1(x),$ where $u_1(x)$ is an arbitrary ambiguity image, and $$HOT_{n+1}(f_0) = \sum_{i=1}^{m} \sum_{j>i, j \in N_i} \int_{\Gamma_{i,j}} |f_i - f_j| ds. \quad \text{EQUATION 120}$$

Hence, $$\min_{f = f_0 + u_1} HOT_{n+1}(f) = \sum_{i=1}^{m} \sum_{j>i, j \in N_i} \int_{\Gamma_{i,j}} |f_i - f_j| ds. \quad \text{EQUATION 121}$$

Because $$HOT_{n+1}(h) = \min_{f = f_0 + u} HOT_{n+1}(f),$$

we have $$\int_{\Omega_a} \min \left\{ \sqrt{\sum_{r=0}^{n+1} \left( \frac{\partial^{n-1} h}{\partial x_1^r \partial x_2^{n+1-r}} \right)^2}, \right. \quad \text{EQUATION 122}$$

$$\left. \sqrt{\left( \frac{\partial h}{\partial x_1} \right)^2 + \left( \frac{\partial h}{\partial x_2} \right)^2} \right\} dx = 0.$$

Therefore, $$\min \left\{ \sqrt{\sum_{r=0}^{n+1} \left( \frac{\partial^{n+1} h}{\partial x_1^r \partial x_2^{n+1-r}} \right)^2}, \sqrt{\left( \frac{\partial h}{\partial x_1} \right)^2 + \left( \frac{\partial h}{\partial x_2} \right)^2} \right\} = 0, \quad \text{EQ. 123}$$

$$\text{for } x \in \Omega_a \setminus \bigcup_{i=1}^{m} \bigcup_{j>i, j \in N_i} \Gamma_{i,j}.$$

That is, $$\left( \frac{\partial h}{\partial x_1} \right)^2 + \left( \frac{\partial h}{\partial x_2} \right)^2 = 0 \text{ or } \sum_{r=0}^{n+1} \left( \frac{\partial^{n+1} h}{\partial x_1^r \partial x_2^{n-1-r}} \right)^2 = 0, \quad \text{EQ. 124}$$

$$\text{for } x \in \Omega_a \setminus \bigcup_{i=1}^{m} \bigcup_{j>i, j \in N_i} \Gamma_{i,j}.$$

We assert that $$\sum_{r=0}^{n+1} \left( \frac{\partial^{n+1} h}{\partial x_1^r \partial x_2^{n+1-r}} \right)^2 = 0, \quad \text{EQUATION 125}$$

$$\text{for } x = (x_1, x_2) \in \Omega_a \setminus \bigcup_{i=1}^{m} \bigcup_{j>i, j \in N_i} \Gamma_{i,j}.$$

Otherwise, there must exist some $$x_0 \in \Omega_a \setminus \bigcup_{i=1}^{m} \bigcup_{j>i, j \in N_i} \Gamma_{i,j}$$

such that $$\sum_{r=0}^{n+1} \left( \frac{\partial^{n+1} h}{\partial x_1^r \partial x_2^{n+1-r}} \right)^2 > 0. \quad \text{EQUATION 126}$$

By continuity, there exists a neighborhood of $x_0$ denoted by $\Omega_{x_0}$ such that $$\Omega_{x_0} \subset \Omega_a \setminus \bigcup_{i=1}^{m} \bigcup_{j>i, j \in N_i} \Gamma_{i,j}, \quad \text{EQUATION 127}$$

$$\text{and} \sum_{r=0}^{n+1} \left( \frac{\partial^{n+1} h}{\partial x_1^r \partial x_2^{n+1-r}} \right)^2 > 0, \text{ for } x \in \Omega_{x_0}. \quad \text{EQUATION 128}$$

By EQUATION 124, we have $$\left( \frac{\partial h}{\partial x_1} \right)^2 + \left( \frac{\partial h}{\partial x_2} \right)^2 = 0, \text{ for } x \in \Omega_{x_0}, \quad \text{EQUATION 129}$$

$$\text{e.g., } \frac{\partial h}{\partial x_1} = \frac{\partial h}{\partial x_2} = 0, \text{ for } x \in \Omega_{x_0}. \quad \text{EQUATION 130}$$

Therefore, $$\frac{\partial^{n+1} h}{\partial x_1^r \partial x_2^{n+1-r}} = 0, \text{ for } x \in \Omega_{x_0}, 0 \le r \le n+1, \quad \text{EQUATION 131}$$

which leads to $$\sum_{r=0}^{n+1} \left( \frac{\partial^{n+1} h}{\partial x_1^r \partial x_2^{n+1-r}} \right)^2 = 0, \text{ for } x \in \Omega_{x_0},. \quad \text{EQUATION 132}$$

This is in contradiction to EQUATION 128. EQUATION 125 implies that $$\frac{\partial^{n+1} h}{\partial x_1^r \partial x_2^{n+1-r}}(x) = 0, \quad \text{EQUATION 133}$$

$$\text{for } x \in \Omega_a \setminus \bigcup_{i=1}^{m} \bigcup_{j>i, j \in N_i} \Gamma_{i,j}, 0 \le r \le n+1.$$

Because $f_0(x)$ is a piecewise n-th (n≥1) order polynomial function in $\Omega_a$, it follows from EQUATION 133 that $$\frac{\partial^{n+1} u}{\partial x_1^r \partial x_2^{n+1-r}}(x) = 0, \quad \text{EQUATION 134}$$

$$\text{for } x \in \Omega_a \setminus \bigcup_{i=1}^{m} \bigcup_{j>i, j \in N_i} \Gamma_{i,j}, 0 \le r \le n+1.$$

Due to the analyticity of u(x) by Theorem 2, we have $$\frac{\partial^{n+1} u}{\partial x_1^r \partial x_2^{n+1-r}}(x) = 0, \text{ for } x \in \Omega_a, 0 \le r \le n+1. \quad \text{EQUATION 135}$$

Hence, u(x) is a n-th (n≥1) order polynomial function in $\Omega_a$. By Theorem 3, we obtain u(x)=0 and h(x)=$f_0$(x).

In conclusion, by analytic continuation interior CT reconstruction technique has been extended from CT to that for SPECT. The uniqueness and stability of interior SPECT have been analyzed. Using the SVD technique, we have implemented an interior SPECT algorithm. Both theoretical analysis and numerical simulations have demonstrated the feasibility of embodiments of the inventive interior SPECT approach.

To facilitate a better understanding of the present invention, the following examples of certain aspects of some embodiments are given. In no way should the following examples be read to limit, or define, the scope of the invention.

EXAMPLES

Example 1

To verify and showcase the inventive interior reconstruction for SPECT of the present invention, we performed several numerical tests. In our simulation, a modified Shepp-Logan phantom of SPECT version was employed inside a circular support $\Omega$ of radius 10 cm. As shown in FIG. 6A, the phantom consists of 10 ellipses whose parameters are the same as that given by Noo et al. We assumed that a uniform attenuation coefficient μ0 throughout the whole support of the phantom. In parallel-beam geometry, 360 view angles were uniformly sampled for an angle range [0,π]. For each view-angle, there were totally 600 detector elements uniformly distributed along a 20 cm linear detector array. For different attenuation coefficients μ0 (0.0 cm$^{-1}$, 0.15 cm$^{-1}$, 0.30 cm$^{-1}$), we analytically computed non-truncated projection datasets. Hence, the backprojection of differential data can be easily calculated at any point to simulate different fields of view (FOVs). Without loss of generality, here we assumed a rectangular FOV and the distribution function $f$(x) was known in the stripe region in the FOV (FIG. 6B). We implemented the TSVD method described in Section 3.2 to reconstruct the distribution image $f$(x) in the whole FOV. The constant parameter ε was set to be 0.02 and there were 512 uniform sampling points along each 20 cm side length in the image space. In the reconstructed procedure, the prior information of $f$(x) in the strip region was chosen as that reconstructed from the non-truncated data with $\mu_0$=0. The reconstructed results are presented in FIG. 7. Because there was noise in the prior information, we had some errors in the reconstructed images, especially in the case $\mu_0$=0.30 cm$^{-1}$. These results are consistent with our aforementioned stability analysis. To verify the stability of the inventive techniques, we added 1% Gaussian white noise into the raw projection data and repeated the above testing steps. The reconstructed images are also presented in FIG. 7, which also support our analysis on the exactness and stability discussed in this application.

Example 2

To verify our theoretical findings obtained in the present invention, we developed a HOT minimization based interior SPECT algorithm in an iterative framework. This algorithm is a modification of our previously reported HOT minimization based on an interior tomography algorithm. One difference between this algorithm and previous algorithms lies in the formulations for the steepest gradient of HOT and the ordered-subset simultaneous algebraic reconstruction technique (OS-SART). Let $f_{u,v}=f(u\Delta,v\Delta)$ be a digital image reconstructed from the available local projections, where $\Delta$ represents the sampling interval, u and v are integers. To demonstrate the computation for the steepest gradient direction, here we use the piecewise-linear case as an example. From the definition of $HOT_2$, $$HOT_2 = \sum_{i=1}^{m} \sum_{j>i, j \in N_i} \int_{\Gamma_{i,j}} |f_i - f_j| ds + \qquad \text{EQUATION 136}$$

$$\int_{\Omega_a} \min \left\{ \sqrt{\sum_{r=0}^{2} \left( \frac{\partial^2 f}{\partial x_1^r \partial x_2^{2-r}} \right)^2}, \sqrt{\left( \frac{\partial f}{\partial x_1} \right)^2 + \left( \frac{\partial f}{\partial x_2} \right)^2} \right\} dx,$$

which consists of the terms for characterizing discontinuities between neighboring regions and also high order derivatives. The first term of $HOT_2$ is for discontinuities between neighboring regions. These discontinuities are due to the jumps of image intensities. In the discretization, the first term of $HOT_2$ would be implemented as the difference of neighboring pixel values, which is proportional to the finite difference in image intensities at relevant pixels. Therefore, we implemented HOT, as follows:

$$HOT_2^{DIS} \Delta^2 \sum_{u,v} \min \qquad \text{EQUATION 137}$$

$$\left\{ \sqrt{\left( \frac{D_{11}(u,v)}{\Delta^2} \right)^2 + \left( \frac{D_{12}(u,v)}{\Delta^2} \right)^2 + \left( \frac{D_{22}(u,v)}{\Delta^2} \right)^2}, \sqrt{\left( \frac{D_1(u,v)}{\Delta} \right)^2 + \left( \frac{D_2(u,v)}{\Delta} \right)^2} \right\} =$$

$$\sum_{u,v} \min \left\{ \sqrt{(D_{11}(u,v))^2 + (D_{12}(u,v))^2 + (D_{22}(u,v))^2}, \sqrt{(D_1(u,v))^2 + (D_2(u,v))^2} \right\},$$

where the intensity differences from the first term of HOT, have been incorporated, $D_{11}(u,v)=f_{u+1,v}+f_{u-1,v}-2f_{u,v}$, $D_{12}(u,v)=(f_{u+1,v+1}+f_{u-1,v-1}-f_{u-1,v+1}-f_{u-1,v-1})/4$, $D_{22}(u,v)=f_{u,v+1}+f_{u,v-1}-2f_{u,v}$, $D_1(u,v)=f_{u+1,v}-f_{u,v}$, $D_2(u,v)=f_{u,v+1}-f_{u,v}$, are the second order and first order finite differences along the coordinate directions, for i,j=1,2, respectively. There are different orders of discontinuities in the image intensity (i.e., pixel values), first order derivatives, and second order derivatives, etc., which HOT combine in a certain way. Numerically, higher order finite differences dominate lower order ones in quantifying discontinuities. Therefore, instead of the above discretization $HOT_2^{DIS}$, we used the following approximation for $HOT_2$:

$$HOT_2^{dis} = \qquad \text{EQUATION 138}$$

$$\sum_{u,v} \sqrt{(D_{11}(u,v))^2 + (D_{12}(u,v))^2 + (D_{22}(u,v))^2},$$

where the first order finite differences have been ignored. The experimental results demonstrated that this was a reasonable approximation in this study. Denote $$G(u,v) = \sqrt{(D_{11}(u,v))^2 + (D_{12}(u,v))^2 + (D_{22}(u,v))^2}, \qquad \text{EQUATION 139}$$

it is easy to verify that $$\frac{\partial HOT_2^{dis}}{\partial f_{u,v}} = \frac{D_{11}(u-1,v)}{G(u-1,v)} + \frac{D_{11}(u+1,v)}{G(u+1,v)} + \frac{D_{22}(u,v-1)}{G(u,v-1)} + \qquad \text{EQ. 140}$$

$$\frac{D_{22}(u,v+1)}{G(u,v+1)} + \frac{1}{4} \left( \frac{D_{12}(u-1,v-1)}{G(u-1,v-1)} + \frac{D_{12}(u+1,v+1)}{G(u+1,v+1)} - \right.$$

$$\left. \frac{D_{12}(u-1,v+1)}{G(u-1,v+1)} - \frac{D_{12}(u+1,v-1)}{G(u+1,v-1)} \right) -$$

$$\frac{2(D_{11}(u,v) + D_{22}(u,v))}{G(u,v)}.$$

For CT scanning systems, the discrete model of projections in terms of Radon transform can are expressed as:

$$Af=b, \qquad \text{EQUATION 141}$$

where data $b=(b_1, \ldots, b_M) \in R^M$ represents the measured projections and each $b_m$ is a x-ray path, 1D vector $f=(f_1, \ldots, f_N) \in R^N$ reformatted from 2D image $f_{u,v}$, and a known non-zero matrix $A=(a_{mn})$ whose component $a_{mn}$ is the intersection area between the $m^{th}$ x-ray path and $n^{th}$ pixel. The SART solution is:

$$f_n^{(k+1)} = f_n^{(k)} + \lambda_k \frac{1}{a_{+n}} \sum_{m=1}^{M} \frac{a_{mn}}{a_{m+}} (b_m - A_m f^{(k)}), \qquad \text{EQUATION 142}$$

where k is the iteration number, $\lambda$ is a relax parameter, and we require that $$a_{m+} \equiv \sum_{n=1}^{N} a_{mn} \neq 0, m = 1, \ldots, M, \qquad \text{EQUATION 143}$$

$$a_{+n} \equiv \sum_{m=1}^{M} a_{mn} \neq 0, n = 1, \ldots, N.$$

Considering the attenuation Radon transform of SPECT as expressed by EQUATION 59, EQUATION 139 can be modified as:

$$\tilde{A}f=b, \qquad \text{EQUATION 144}$$

with $\tilde{A}=(a_{mn}w_{mn}^{\mu_0})$, where $w_{mn}^{\mu_0}$ is the corresponding discrete term $e^{\mu_0 t}$ in EQUATION 59 and the SART solution for SPECT can be expressed as:

$$f_n^{(k+1)} = f_n^{(k)} + \lambda_k \frac{1}{a_{-n}} \sum_{m=1}^{M} \frac{a_{mn}}{\tilde{a}_{m+}} (b_m - \tilde{A}_m f^{(k)}),$$ EQUATION 145

$$\tilde{a}_{m+} \equiv \sum_{n=1}^{N} a_{mn} w_{mn}^{\mu_0} \neq 0, m = 1, \ldots ,$$ EQUATION 146

$$M, a_{+n} \equiv \sum_{m=1}^{M} a_{mn} \neq 0, n = 1, \ldots , N.$$

Clearly, the CT reconstruction formula is the special case $\mu_0=0$ of the SPECT solution. Because key details of our algorithm were already reported, here we omit the implementation steps for simplification.

In our numerical simulation, we assumed a popular parallel-beam imaging geometry in the SPECT field. All other imaging geometry parameters and reconstruction control parameters are well known in the art. At the origin, we assumed a disk-shaped compact support of radius 100 mm with a uniformly attenuation coefficient $\mu_0$. Inside the compact support, there is a modified and piecewise linear Shepp-Logan phantom. Representative reconstructed images are shown in FIGS. 12 & 13. As seen from FIGS. 12 and 13, the reconstructed SPECT images using the inventive HOT minimization algorithm are in an excellent agreement with the truth inside the ROI. However, it can be observed that the profiles near the edges deviate substantially from the truth. Although a rigorous stability analysis has not been performed yet, it is conjectured that this phenomenon is a stability issue of interior tomography. We believe that this behavior is similar to what we analyzed for the knowledge based interior CT. The closer the distance to the peripheral region of an ROI, the less the stability of the interior reconstruction. A different numerical implementation could reduce this discrepancy. However, it cannot be completely removed unless stronger prior knowledge is incorporated for interior reconstruction.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. It is intended that the specification and examples be considered as exemplary in nature and that variations that do not depart from the essence of the invention are intended to be within the scope of the invention.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Noo F, Clackdoyle R, Pack J D. A two-step Hilbert transform method for 2D image reconstruction. *Physics in Medicine and Biology* 2004; 49(17):3903-3923.

Defrise M et al. Truncated Hilbert transform and image reconstruction from limited tomographic data. *Inverse Problems* 2006; 22(3):1037-1053.

Wang G, Ye Y B, Yu H Y. General VOI/ROI reconstruction methods and systems using a truncated Hilbert transform (Patent disclosure submitted to Virginia Tech. Intellectual Properties on 15 May 2007), 2007.

Ye Y B, Yu H Y, Wei Y C, Wang G. A general local reconstruction approach based on a truncated Hilbert transform. *International Journal of Biomedical Imaging* 2007; 2007: 8. Article ID: 63634.

Ye Y B, Yu H Y, Wang G. Exact interior reconstruction with cone-beam CT. *International Journal of Biomedical Imaging* 2007; 2007:5. Article ID: 10693.

Ye Y B, Yu H Y, Wang G. Exact interior reconstruction from truncated limited-angle projection data. *International Journal of Biomedical Imaging* 2008; 2008:6. Article ID: 427989.

Natterer F. The mathematics of computerized tomography. *Classics in Applied Mathematics*. Society for Industrial and Applied Mathematics: Philadelphia, 2001.

Kudo H et al. Tiny a priori knowledge solves the interior problem. 2007 *IEEE Nuclear Science Symposium and Medical Imaging*, Honolulu, Hi., 28 Oct.-3 Nov. 2007; 4068-4075. Paper No.: M21-1.

Kudo H et al. Tiny a priori knowledge solves the interior problem in computed tomography. *Physics in Medicine and Biology* 2008; 53(9):2207-2231.

Li T et al. An efficient reconstruction method for nonuniform attenuation compensation in nonparallel beam geometries based on Novikov's explicit inversion formula. *IEEE Transactions on Medical Imaging* 2005; 24(10):1357-1368.

Tang Q L et al. Exact fan-beam and 4 pi-acquisition cone-beam SPECT algorithms with uniform attenuation correction. *Medical Physics* 2005; 32(11):3440-3447.

Tang Q L, Zeng G S L, Gullberg G T. Analytical fan-beam and cone-beam reconstruction algorithms with uniform attenuation correction for SPECT. *Physics in Medicine and Biology* 2005; 50(13):3153-3170.

Noo F et al. Image reconstruction from truncated data in single-photon emission computed tomography with uniform attenuation. *Inverse Problems* 2007; 23(2):645-667.

Rullgard H. An explicit inversion formula for the exponential Radon transform using data from 180 degrees. *Arkiv f" or Matematik* 2004; 42:353-362.

Rullgard H. Stability of the inverse problem for the attenuated Radon transform with 180 degrees data. *Inverse. Problems* 2004; 20(3):781-797.

Courdurier M. Restricted measurements for the X-ray transform. *Doctoral Dissertation*, University of Washington, Seattle, 2007.

Nevanlinna R (ed.). *Eindentige Analytische Functionen* (2nd edn). Grundlehren der mathematischen Wissenschaften, vol. 46. Springer: Berlin, 1953.

Yu H Y, Wang G. Studies on implementation of the Katsevich algorithm for spiral cone-beam CT. *Journal of X-ray Science and Technology* 2004; 12(2):96-117.

Hansen P C. Truncated singular value decomposition solutions to discrete ill-posed problems with ill-determined numerical rank. *SIAM Journal on Scientific and Statistical Computing* 1990; 11(3):503-518.

Hansen P C. Regularization, GSVD and truncated GSVD. *BIT* 1989; 29(3):491-504.

Ramachandran P A. Method of fundamental solutions: singular value decomposition analysis. *Communications in Numerical Methods in Engineering* 2002; 18(11):789-801.

Ye Y B, Zhao S Y, Yu H Y, Wang G. Exact reconstruction for cone-beam scanning along nonstandard spirals and other curves. *Developments in X-Ray Tomography IV, Proceedings of SPIE*, Denver, Colo., U.S.A., vol. 5535, 4-6 Aug. 2004; 293-300.

Ye Y B, Zhao S Y, Yu H Y, Wang G. A general exact reconstruction for cone-beam CT via backprojection-filtration. *IEEE Transactions on Medical Imaging* 2005; 24(9):1190-1198.

Natterer F, Wubbeling F (eds). *Mathematical Methods in Image Reconstruction*. Society for Industrial and Applied Mathematics: Philadelphia, 2001.

H. Y. Yu, J. S. Yang, M. Jiang and G. Wang, *Interior SPECT-exact and stable ROI reconstruction from uniformly attenuated local projections*. Communications in Numerical Methods in Engineering, 2009. 25(6): p. 693-710.

Q. Huang et al., *Reconstruction from uniformly attenuated SPECT projection data using the DBH method*. IEEE Transactions on Medical Imaging, 2009. 28(1): p. 17-29.

G. S. L. Zeng, and G. T. Gullberg, *Exact emission SPECT reconstruction with truncated transmission data*. Physics in Medicine and Biology, 2009. 54(11): p. 3329-3340.

H. Y. Yu, Y. B. Ye, and G. Wang, *Local reconstruction using the truncated Hilbert transform via singular value decomposition*. Journal of X-Ray Science and Technology, 2008. 16(4): p. 243-251.

M. Courdurier, et al., *Solving the interior problem of computed tomography using a priori knowledge*. Inverse Problems, 2008. 24, Article ID 065001, 27 pages.

G. Wang, and H. Y. Yu, *Methods and systems for exact local CT based on compressive sampling*, Patent disclosure submitted to Virginia Tech. Intellectual Properties on December 20, Editor. 2008.

E. J. Candes, and J. Romberg. *Signal recovery from random projections*. in Computational Imaging III, Proceedings of SPIE Vol. 5764. 2005.

D. L. Donoho, *Compressed sensing*. IEEE Transactions on Information Theory, 2006. 52(4): p. 1289-1306.

E. J. Candes, J. Romberg, and T. Tao, *Robust uncertainty principles: Exact signal reconstruction from highly incomplete frequency information*. IEEE Transactions on Information Theory, 2006. 52(2): p. 489-509.

H. Y. Yu, and G. Wang, *Compressed sensing based Interior tomography*. Phys Med Biol, 2009. 54(9): p. 2791-2805.

H. Y. Yu, J. S. Yang, M. Jiang and G. Wang, *Supplemental analysis on compressed sensing based interior tomography*. Phys Med Biol, 2009. 54(18): p. N425-N432.

W. M. Han, H. Y. Yu, and G. Wang, *A total variation minimization theorem for compressed sensing based tomography*. International Journal of Biomedical Imaging, 2009, Article ID:125871, 3 pages.

J. S. Yang, H. Y. Yu, M. Jiang and G. Wang, *High-order total variation minimization for interior tomography*. Inverse Problems, 2010. 26(3): p. 29.

C. Hamaker, et al., *The Divergent beam X-ray transform*. Rocky Mountain Journal of Mathematics, 1980. 10(1): p. 253-283.

O. Tretiak, and C. Metz, *The exponential Radon-transform*. SIAM Journal on Applied Mathematics, 1980. 39(2): p. 341-354.

E. C. Titchmarsh, *Introduction to the Theory of Fourier Integrals*. 1937: Oxford: The Clarendon Press G. Wang, and M. Jiang, *Ordered-subset simultaneous algebraic reconstruction techniques (OS-SART)*. Journal of X-ray Science and Technology, 2004. 12(3): p. 169-177.

A. Harten, et al., *Uniformly high order accurate essentially non-oscillatory schemes* 3. Journal of Computational Physics, 1987. 71(2): p. 231-303.

G. Wang, H. Y. Yu, and Y. B. Ye, *A scheme for multi-source interior tomography*. Med Phys, 2009. 36(8): p. 3575-3581.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. It is intended that the specification and examples be considered as exemplary in nature and that variations that do not depart from the essence of the invention are intended to be within the scope of the invention.

Throughout this application, various publications are referenced. The disclosures of these publications in their entireties are hereby incorporated by reference into this application in order to more fully describe the features of the invention and/or the state of the art to which this pertains. The references disclosed are also individually and specifically incorporated by reference herein for the material contained in them that is discussed in the portion of this disclosure in which the reference is relied upon.

The invention claimed is:

1. A theoretically exact local reconstruction method comprising reconstructing a region of interest (ROI) of an object into an image from local single photon emission computed tomography (SPECT) projection data of the ROI by modeling the projection data as an attenuated Radon transform comprising formula:

$$P_o(\theta, s) = \int_{-\infty}^{\infty} f(s\theta + t\theta^\perp) e^{-\int_t^\infty \mu(s\theta + \tilde{t}\theta^\perp) d\tilde{t}} dt,$$

where $P_o$ represents the original projection data, f(x) is the image to be reconstructed, $\theta$=(cos $\theta$, sin ($\theta$)), $\theta^\perp$=(−sin $\theta$, cos ($\theta$)), and μ(x) is the attenuation coefficient map.

2. The method of claim 1, further comprising:
defining a compact support and the corresponding attenuation coefficient; and measuring the attenuated Radon transform of the projection data through the ROI.

3. The method of claim 2, further comprising:
modeling the region of interest as piecewise polynomial; and reconstructing the image by performing a high order TV minimization while minimizing the data discrepancy.

4. The method of claim 3, wherein the high order TV is minimized by steepest descent searching method.

5. The method of claim 3, wherein the high order TV is minimized by soft-threshold filtering method.

6. The method of claim 2, further comprising:
identifying a known subregion inside the region of interest; backprojecting the derivative data to a PI line passing through the known subregion; and reconstructing the image by inverting the generalized truncated Hilbert transform $$g_w(u) = -\frac{g(u)}{2\pi} = PV \int_{c_{sb}}^{c_{se}} ch_{\mu_0}(u - \tilde{u}) f(\tilde{u}) d\tilde{u}, u \in (c_{vb}, c_{ve}).$$

7. The method of claim 6, wherein the generalized truncated Hilbert transform is inverted by singular value decomposition method.

8. The method of claim 6, wherein the generalized truncated Hilbert transform is inverted by projection onto convex set method.

9. The method of claim 1, further comprising scanning an object using a SPECT scanner to acquire projection data relating to the object.

10. The method of claim 1, wherein the single photon emission computed tomography projection data are uniformly attenuated local projections.

11. The method of claim 1, wherein the single photon emission computed tomography projection data are generalized attenuated local projections.

12. The method of claim 1, wherein the attenuation coefficient μ(x) is known on the whole compact support.

13. The method of claim 1, wherein the attenuation coefficient μ(x) is reconstructed from global un-truncated transmission projections.

14. The method of claim 1, wherein the attenuation coefficient μ(x) is reconstructed from local truncated transmission projections passing through the same region of interest.

15. The method of claim 14, wherein the attenuation coefficient μ(x) is known inside a subregion of the region of interest.

16. The method of claim 14, wherein the attenuation coefficient μ(x) is piecewise polynomial inside the region of interest.

17. The method of claim 1, wherein the projection data $P_o(\theta,s)$ is acquired with gamma camera.

18. The method of claim 1, wherein the reconstruction image is reconstructed using guided computed tomography and/or nano-computer tomography.

19. A SPECT system comprising:
a SPECT scanner operably configured for scanning an object that is larger than the field of view (FOV) of the scanner to acquire projection data relating to the object;
a processing module operably configured for theoretically exact local reconstruction for the scanned portion of the object into an image by identifying a region of interest (ROI), computing a generalized Hilbert transform by backprojecting a derivative of the projection data on a portion of a PI-segment inside the ROI, performing a reconstruction method that yields an exact and stable reconstruction; and
a processor for executing the processing module.

20. The system of claim 19, wherein the SPECT scanner and processing module are operably configured for only scanning and reconstructing a heart, lung, head, or neck of a subject.

21. The system of claim 19, wherein the processing module is operably configured for modeling the projection data as an attenuated Radon transform comprising formula:

$$P_o(\theta, s) = \int_{-\infty}^{\infty} f(s\theta + t\theta^\perp) e^{-\int_t^\infty \mu(s\theta + \tilde{t}\theta^\perp) d\tilde{t}} dt,$$

where $P_o$ represents the original projection data, f(x) is the image to be reconstructed, $\theta$=(cos $\theta$, sin ($\theta$)), $\theta^\perp$=(−sin $\theta$, cos ($\theta$)), and μ(x) is the attenuation coefficient map.

22. The system of claim 21, further comprising:
defining a compact support and the corresponding attenuation coefficient; and measuring the attenuated Radon transform of the projection data through the ROI.

23. The system of claim 21, further comprising:
modeling the region of interest as piecewise polynomial; and reconstructing the image by performing a high order TV minimization while minimizing the data discrepancy.

24. The system of claim 23, wherein the high order TV is minimized by steepest descent searching method.

25. The system of claim 23, wherein the high order TV is minimized by soft-threshold filtering method.

26. The system of claim 21, further comprising:
identifying a known subregion inside the region of interest; backprojecting the derivative data to a PI line passing through the known subregion; and reconstructing the image by inverting the generalized truncated Hilbert transform $$g_w(u) = -\frac{g(u)}{2\pi} = PV \int_{c_{sb}}^{c_{se}} ch_{\mu_0}(u - \tilde{u}) f(\tilde{u}) d\tilde{u}, u \in (c_{vb}, c_{ve}).$$

27. The system of claim 26, wherein the generalized truncated Hilbert transform is inverted by singular value decomposition method.

28. The system of claim 26, wherein the generalized truncated Hilbert transform is inverted by projection onto convex set method.

29. The system of claim 19, wherein the reconstruction image is reconstructed using guided computed tomography and/or nano-computer tomography.

30. The system of claim 21, wherein the single photon emission computed tomography projection data are uniformly attenuated local projections.

31. The system of claim 21, wherein the single photon emission computed tomography projection data are generalized attenuated local projections.

32. The system of claim 21, wherein the attenuation coefficient $\mu(x)$ is known on the whole compact support.

33. The system of claim 21, wherein the attenuation coefficient $\mu(x)$ is reconstructed from global un-truncated transmission projections.

34. The system of claim 21, wherein the attenuation coefficient $\mu(x)$ is reconstructed from local truncated transmission projections passing through the same region of interest.

35. The system of claim 34, wherein the attenuation coefficient $\mu(x)$ is known inside a subregion of the region of interest.

36. The system of claim 34, wherein the attenuation coefficient $\mu(x)$ is piecewise polynomial inside the region of interest.

37. The system of claim 21, wherein the projection data $P_o(\theta,s)$ is acquired with gamma camera.

38. A method of using a SPECT scanner to acquire projection data relating to an object, the method comprising:
 imaging an object with a SPECT scanner, wherein the SPECT scanner has a field of view (FOV) smaller than the object;
 acquiring projection data relating to the object by identifying a region of interest (ROI) and computing a generalized Hilbert transform by backprojecting a derivative of the projection data on a portion of a PI-segment inside the ROI;
 and performing a reconstruction method that yields theoretically exact and stable reconstruction into an image for a scanned portion of the object.

* * * * *